United States Patent
Buck

(10) Patent No.: US 9,695,420 B2
(45) Date of Patent: Jul. 4, 2017

(54) ANTIVIRAL THERAPY

(71) Applicant: The University Court of the University of Edinburgh, Edinburgh (GB)

(72) Inventor: Amy Buck, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 14/467,988

(22) Filed: Aug. 25, 2014

(65) Prior Publication Data

US 2016/0340677 A1    Nov. 24, 2016

Related U.S. Application Data

(62) Division of application No. 13/262,086, filed as application No. PCT/GB2010/000623 on Mar. 30, 2010, now Pat. No. 8,815,820.

(30) Foreign Application Priority Data

Mar. 30, 2009   (GB) .................................. 0905485.9

(51) Int. Cl.
```
A61K 48/00      (2006.01)
C07H 21/02      (2006.01)
C07H 21/04      (2006.01)
C12N 15/113     (2010.01)
C12N 15/11      (2006.01)
```
(52) U.S. Cl.
CPC ........ *C12N 15/1131* (2013.01); *C12N 15/111* (2013.01); *C12N 2310/141* (2013.01); *C12N 2320/10* (2013.01); *C12N 2320/30* (2013.01)

(58) Field of Classification Search
CPC ... A61K 48/00; C12N 15/113; C12N 2310/11
See application file for complete search history.

(56) References Cited

FOREIGN PATENT DOCUMENTS

WO     WO 2009/033185 A1    3/2009

OTHER PUBLICATIONS

International Search Report of International Application No. PCT/GB2010/000623, mailed Oct. 1, 2010 (4 pages).
International Preliminary Report on Patentability of International Application No. PCT/GB2010/000623, mailed Oct. 4, 2011 (9 pages).
Barbarotto et al. "MicroRNAs as New Players in the Genomic Galaxy and Disease Puzzles" *Clinical and Translational Science* 1(1):50-56 (2008).
Cullen "Viruses and MicroRNAs" *Nature Genetics* 38:525-530 (2006).
Gottwein et al, "Viral and Cellular MicroRNAs as Determinants of Viral Patnogenesis and Immunity" *Cell Host & Microbe* 3(6):375-387 (2008).
Huang et al. "Cellular MicroRNAs Contribute to HIV-1 Latency in Resting Primary CD4+ T Lymphocytes" *Nature Medicine* 13(10):1241-1247 (2007).
Huang et al. Supplementary Information for "Cellular MicroRNAs Contribute to HIV-1 Latency in Resting Primary CD4+ T Lymphocytes" *Nature Medicine* (29 pages)(2007).
Otsuka et al, "Hypersusceptibility to Vesicular Stomatitis Virus Infection in Dicer1-Deficient Mice is Due to Impaired miR24 and miR93 Expression" *Immunity* 27:123-134 (2007).
Otsuka et al. Supplemental Data for "Hypersusceptibility to Vesicular Stomatitis Virus Infection in Dicer1-Deficient Mice is Due to Impaired miR24 and miR93 Expression" Immunity (7pages)(2007).
Pedersen et al. "MicroRNAs in the Immune Response" *Cytokine* 43:391-394(2008).
Pedersen et al. "Interferon Modulation of Cellular MicroRNAs as an Antiviral Mechanism" *Nature* 449(7164):919-923 (2007).
Sonkoly et al. "MicroRNAs and Immunity: Novel Players in the Regulation of Normal Immune Function and Inflammation" *Seminars in Cancer Biology* 18:131-140 (2008).
Ahluwalia et al. "Human cellular microRNA has-miR-29a interferes with viral nef protein expression and HIV-I replication" *Retrovirology* 5(117):1-10 (2008).
Angulo et al. "The Major Immediate-Early Gene *ie3* of Mouse Cytomegalovirus Is Essential for Viral Growth" *Journal of Virology* 74(23):11129-11136 (2000).
Bartel, David P. "MicroRNAs: Genomics, Biogenesis, Mechanism, and Function" *Cell* 116:281-297 (2004).
Birmingham et al. "Statistical Methods for Analysis of High-Throughput RNA Interference Screens" *Nature Methods* 6(8):569-575 (2009).
Breitling et al. "Rank products: a simple, yet powerful, new method to detect differentially regulated genes in replicated microarray experiments" *FEBS Letters* 573:83-92 (2004).
Buck et al. "Discrete Clusters of Virus-Encoded MicroRNAs Are Associated with Complementary Strands of the Genome and the 7.2-Kilobase Stable Intron in Murine Cytomegalovirus" *Journal of Virology* 81(24):13761-13770 (2007).
Buck et al. "Post-transcriptional regulation of miR-27 in murine cytomegalovirus infection" *RNA* 16:307-315 (2010).
Chang et al. "microRNAs in Vertebrate Physiology and Human Disease" *Annual Review of Genomics and Human Genetics* 8:215-239 (2007).
Dutia et al. "Identification of a region of the virus genome involved in murine gammaherpesvirus 68-induced splenic pathology" *Journal of General Virology* 85:1393-1400 (2004).
Ghosh et al. "Cellular versus viral microRNAs in host-virus interaction" *Nucleic Acids Research* 37(4):1035-1048 (2009).
Giraldez et al. "Zebrafish MiR-430 Promotes Deadenylation and Clearance of Maternal mRNAs" *Science* 312(5770):75-79 (2006).

(Continued)

*Primary Examiner* — Amy Bowman
(74) *Attorney, Agent, or Firm* — Myers Bigel, P.A.

(57) ABSTRACT

The present invention provides a method of identifying host cell molecules which may be modulated to inhibit viral replication and method of testing antiviral compounds. In addition, the invention provides compositions, methods and medicaments for treating viral infections and/or diseases or conditions caused or contributed to by viruses.

4 Claims, 24 Drawing Sheets

(56) References Cited

OTHER PUBLICATIONS

Jopling et al. "Modulation of Hepatitis C Virus RNA Abundance by a Liver-Specific MicroRNA" *Science* 309(5740):1577-1581 (2005).

Jopling et al. "Positive and Negative Modulation of Viral and Cellular mRNAs by Liver-specific MicroRNA miR-122" *Cold Spring Harbor Symposia on Quantitative Biology* 71:369-376 (2006).

Kumar, Ajit "RNA interference: a multifaceted innate antiviral defense" *Retrovirology* 5(17):1-4 (2008).

Lecellier et al. "A Cellular MicroRNA Mediates Antiviral Defense in Human Cells" *Science* 308(5721):557-560 (2005).

Lee et al. "The C. elegans Heterochronic Gene *lin*-4 Encodes Small RNAs with Antisense Complementarity to *lin*-14" *Cell* 75:843-854 (1993).

Lewis et al. "Conserved Seed Pairing, Often Flanked by Adenosines, Indicates that Thousands of Human Genes are MicroRNA Targets" *Cell* 120:15-20 (2005).

Mahajan et al. "Virus-specific host miRNAs: antiviral defenses or promoters or persistent infection?" *Trends in Immunology* 30(1):1-7 (2009).

Manning et al. "Insertional Mutagenesis of the Murine Cytomegalovirus Genome: One Prominent α Gene (ie2) Is Dispensable for Growth" *Virology* 167:477-484 (1988).

Martinez et al. "Human papillomavirus type 16 reduces the expression of microRNA-218 in cervical carcinoma cells" *Oncogene* 27(18):2575-2582 (2008).

McGeoch et al. "Molecular Phylogeny and Evolutionary Timescale for the Family of Mammalian Herpesviruses" *Journal of Molecular Biology* 247:443-458 (1995).

Murakami et al. "Regulation of the hepatitis C virus genome replication by miR-199a" *Journal of Hepatology* 50:453-460 (2009).

Nathans et al. "Cellular microRNA and P-bodies modulate host-HIV-1 interactions" *Molecular Cell* 34(6):696-709 (2009).

Parameswaran et al. "Six RNA Viruses and Forty-One Hosts: Viral Small RNAs and Modulation of Small RNA Repertoires in Vertebrate and Invertebrate Systems" *PLoS Pathogens* 6(2):e1000764 (2010).

Sun et al. "Immediate-Early Expression of the Herpes Simplex Virus Type 1 ICP27 Transcript Is Not Critical for Efficient Replication In Vitro or In Vivo" *Journal of Virology* 78(19):10470-10478 (2004).

Sunil-Chandra et al. "Virological and pathological features of mice infected with murine gammaherpesvirus 68" *Journal of General Virology* 73:2347-2356 (1992).

Triboulet et al. "Suppression of MicroRNA-Silencing Pathway by HIV-1 during Virus Replication" *Science* 315(5818):1579-1582 (2007).

Wang et al. "Human Cytomegalovirus Infection Alters the Expression of Cellular MicroRNA Species That Affect Its Replication" *Journal of Virology* 82(18):9065-9074 (2008).

Winter et al. "Many roads to maturity: microRNA biogenesis pathways and their regulation" *Nature Cell Biology* 11(3):228-234 (2009).

Yeung et al. "Roles for microRNAs, miR-93 and miR-130b, and TP53INP1 tumor suppressor in cell growth dysregulation by HTLV-1" *Cancer Research* 68(21):8976-8985 (2008).

SEQUENCE LISTING

```
<160> NUMBER OF SEQ ID NOS: 26

<210> SEQ ID NO 1
<211> LENGTH: 22
<212> TYPE: RNA
<213> ORGANISM: Mus musculus

<400> SEQUENCE: 1
uagcagcacg uaaauauugg cg                                                22

<210> SEQ ID NO 2
<211> LENGTH: 22
<212> TYPE: RNA
<213> ORGANISM: Mus musculus

<400> SEQUENCE: 2
cuuucagucg gauguuugca gc                                                22

<210> SEQ ID NO 3
<211> LENGTH: 22
<212> TYPE: RNA
<213> ORGANISM: Mus musculus

<400> SEQUENCE: 3
aaggagcuca cagucuauug ag                                                22

<210> SEQ ID NO 4
<211> LENGTH: 21
<212> TYPE: RNA
<213> ORGANISM: Mus musculus

<400> SEQUENCE: 4
ucacagugaa ccggucucuu u                                                 21

<210> SEQ ID NO 5
```

```
<211> LENGTH: 21
<212> TYPE: RNA
<213> ORGANISM: Mus musculus

<400> SEQUENCE: 5
cuuuuugcgg ucugggcuug c                                              21

<210> SEQ ID NO 6
<211> LENGTH: 22
<212> TYPE: RNA
<213> ORGANISM: Mus musculus

<400> SEQUENCE: 6
gcugaccccu aguccagugc uu                                             22

<210> SEQ ID NO 7
<211> LENGTH: 21
<212> TYPE: RNA
<213> ORGANISM: Mus musculus

<400> SEQUENCE: 7
agcuacaucu ggcuacuggg u                                              21

<210> SEQ ID NO 8
<211> LENGTH: 22
<212> TYPE: RNA
<213> ORGANISM: Mus musculus

<400> SEQUENCE: 8
ugucaguuug ucaaauaccc ca                                             22

<210> SEQ ID NO 9
<211> LENGTH: 23
<212> TYPE: RNA
<213> ORGANISM: Mus musculus

<400> SEQUENCE: 9
uuaaugcuaa uugugauagg ggu                                            23

<210> SEQ ID NO 10
<211> LENGTH: 21
<212> TYPE: RNA
<213> ORGANISM: Mus musculus

<400> SEQUENCE: 10
uucacagugg cuaaguucug c                                              21

<210> SEQ ID NO 11
<211> LENGTH: 23
<212> TYPE: RNA
<213> ORGANISM: Mus musculus

<400> SEQUENCE: 11
agcagcauug uacagggcua uga                                            23

<210> SEQ ID NO 12
<211> LENGTH: 23
<212> TYPE: RNA
<213> ORGANISM: Mus musculus

<400> SEQUENCE: 12
ugucugcccg agugccugcc ucu                                            23
```

```
<210> SEQ ID NO 13
<211> LENGTH: 19
<212> TYPE: RNA
<213> ORGANISM: Mus musculus

<400> SEQUENCE: 13
cucggggauc aucauguca                                              19

<210> SEQ ID NO 14
<211> LENGTH: 20
<212> TYPE: RNA
<213> ORGANISM: Mus musculus

<400> SEQUENCE: 14
uacaguaguc ugcacauugg                                             20

<210> SEQ ID NO 15
<211> LENGTH: 20
<212> TYPE: RNA
<213> ORGANISM: Mus musculus

<400> SEQUENCE: 15
uggcucaguu cagcaggaac                                             20

<210> SEQ ID NO 16
<211> LENGTH: 19
<212> TYPE: RNA
<213> ORGANISM: Mus musculus

<400> SEQUENCE: 16
uaaggcacgc ggugaaugc                                              19

<210> SEQ ID NO 17
<211> LENGTH: 21
<212> TYPE: RNA
<213> ORGANISM: Mus musculus

<400> SEQUENCE: 17
uaggcagugu aauuagcuga u                                           21

<210> SEQ ID NO 18
<211> LENGTH: 20
<212> TYPE: RNA
<213> ORGANISM: Mus musculus

<400> SEQUENCE: 18
uguuugcaga ggaaacugag                                             20

<210> SEQ ID NO 19
<211> LENGTH: 22
<212> TYPE: RNA
<213> ORGANISM: Mus musculus

<400> SEQUENCE: 19
acagcaggca cagacaggca gu                                          22

<210> SEQ ID NO 20
<211> LENGTH: 23
<212> TYPE: RNA
<213> ORGANISM: Mus musculus

<400> SEQUENCE: 20
agcagcauug uacagggcua uca                                         23
```

```
<210> SEQ ID NO 21
<211> LENGTH: 22
<212> TYPE: RNA
<213> ORGANISM: Mus musculus

<400> SEQUENCE: 21
ugcggggcua gggcuaacag ca                                              22

<210> SEQ ID NO 22
<211> LENGTH: 20
<212> TYPE: RNA
<213> ORGANISM: Mus musculus

<400> SEQUENCE: 22
uguaaacauc cucgacugga                                                 20

<210> SEQ ID NO 23
<211> LENGTH: 20
<212> TYPE: RNA
<213> ORGANISM: Mus musculus

<400> SEQUENCE: 23
uguaaacauc cuacacucag                                                 20

<210> SEQ ID NO 24
<211> LENGTH: 21
<212> TYPE: RNA
<213> ORGANISM: Mus musculus

<400> SEQUENCE: 24
uguaaacauc cuacacucuc a                                               21

<210> SEQ ID NO 25
<211> LENGTH: 20
<212> TYPE: RNA
<213> ORGANISM: Mus musculus

<400> SEQUENCE: 25
uguaaacauc cccgacugga                                                 20

<210> SEQ ID NO 26
<211> LENGTH: 19
<212> TYPE: RNA
<213> ORGANISM: Mus musculus

<400> SEQUENCE: 26
uguaaacauc cuugacugg                                                  19
```

ANTIVIRAL THERAPY

STATEMENT OF PRIORITY

This application is a divisional application of, and claims priority to, U.S. application Ser. No. 13/262,086, now U.S. Pat. No. 8,815,820 which is a 35 U.S.C. §371 national phase application of International Application No. PCT/GB2010/000623, filed Mar. 30, 2010, which claims priority to Great Britain Application No. 0905485.9 filed Mar. 30, 2009, the entire contents of each of which are incorporated by reference herein for their disclosures.

STATEMENT REGARDING ELECTRONIC FILING OF A SEQUENCE LISTING

A Sequence Listing in ASCII text format, submitted under 37 C.F.R. §1.821, entitled 9013-110_ST25.txt, 4,081 bytes in size, generated on Aug. 26, 2014 and filed via EFS-Web, is provided in lieu of a paper copy. This Sequence Listing is hereby incorporated by reference into the specification for its disclosures.

FIELD OF THE INVENTION

The present invention provides a method of identifying host cell molecules which may be modulated to inhibit viral replication and method of testing antiviral compounds. In addition, the invention provides compositions, methods and medicaments for treating viral infections and/or diseases or conditions caused or contributed to by viruses.

BACKGROUND OF THE INVENTION

Antivirals currently on the market use small molecules as the active pharmaceutical ingredient and tend to be specific to certain (types of) viruses. However, through the incorporation of random mutations etc., viruses can easily evade the effects of antivirals targeting viral proteins, or parts of proteins.

MicroRNAs (miRNAs) are small RNAs (22 nt) that regulate eukaryotic gene expression by binding to specific messenger RNA transcripts, causing the mRNAs to be degraded or causing their translation to be repressed (Bartel 2004). MicroRNAs are encoded in the genomes of animals, plants and viruses; these genes are transcribed by RNA polymerase II as part of larger fold-back transcripts (primary miRNAs), which are processed in the nucleus by Drosha family members to form short stem-loops (pre-miRNAs), and then exported to the cytoplasm for processing by a Dicer family member to form the mature miRNA. It is estimated that miRNAs comprise 1% of genes in animals and may target up to 30% of genes in humans (Lewis, Burge et al. 2005). A given microRNA can potentially target hundreds of genes and by modulating a whole network of gene targets, can exert dramatic effects on various cellular processes (Giraldez, Mishima et al. 2006). The mechanism of microRNA function (generally down-regulation of host proteins) is distinct, but perhaps complementary, to other regulatory molecules (e.g. transcription factors). MicroRNAs have been shown to play key roles in cellular proliferation, differentiation, development and neuronal function; specific miRNAs also play a role in cancer formation, cardiovascular and metabolic diseases, and, more recently, viral infection.

MicroRNAs are an important component of viral-host interactions and have been shown to influence the outcome of viral infections, reviewed in (Ghosh, Mallick et al. 2008; Gottwein and Cullen 2008; Kumar 2008). Recent studies have demonstrated that specific host microRNAs are up-or down regulated upon infection with a particular virus and that some of these host microRNAs have target sites against specific viruses. This has led to the suggestion that microRNAs could mediate anti-viral defense; for example, mir-32 was shown to limit the replication of primate foamy virus (PFV) in human cells by targeting regions in the PFV genome (Lecellier, Dunoyer et al. 2005). In another study, mir-24 and mir-93 were shown to target vesicular stomatitis virus, leading to decreased replication of the virus in mice (Otsuka, Jing et al. 2007). However, rather than being "anti-viral", the host microRNAs that target viruses may in fact be exploited by the viruses for persistence. From an evolutionary point of view, if the host miRNA target sites were disadvantageous to the virus, the virus could readily evolve to eliminate these sites (requiring only a single mutation) (Mahaj an, Drake et al. 2008). For example, it was shown that host microRNAs (mir-28, mir-125b, mir-150, mir-223 and mir-382) down regulate HIV mRNA and may be used by the virus to avoid being eliminated by the immune system (Huang, Wang et al. 2007). Furthermore, it is known that the host microRNA—mir-122, can actually be exploited by the virus to upregulate viral genes (by unknown mechanisms) (Jopling, Norman et al. 2006). The work listed above demonstrates that human or mouse microRNAs can play a pro- or anti-viral function by interacting with viral sequences; however, antiviral therapies based on microRNAs that specifically interact with viral genomes possess a number of disadvantages: 1) the viruses can mutate/evolve to escape the microRNA-target interactions 2) the identified microRNAs would be limited to function against the virus with the target site, rather than holding broad anti-viral potential.

More recently, it has been shown that cellular microRNAs that are induced or down regulated upon viral infection can also modulate host genes, which are co-factors for viral infection. For example, the miRNA cluster mir-17/92 was shown to be decreased upon HIV-1 infection and was shown with knockdown experiments to effect HIV-1 replication; this microRNA targets histone acetylase protein PCAF, which is a co-factor for the viral Tat protein (Triboulet, Mari et al. 2007).

SUMMARY OF THE INVENTION

The present invention is based on the finding that micro RNA (miRNA) molecules may be exploited as a means of treating viral infections. More specifically, the inventors have discovered that by modulating the expression of one or more host cell miRNA molecules, it is possible to inhibit the replication and/or propagation of one or more viral species in a host cell.

The inventors have observed that when over expressed, certain host cell miRNA molecules may exhibit antiviral effects. When these same host cell miRNA molecules are inhibited, viral propagation and/or replication in the host cell may increase. In other instances, certain host cell miRNA molecules are pro-viral and thus by inhibiting these host cell miRNAs, it is also possible to achieve an antiviral effect.

It should be understood that the definitions of the various terms used in this specification apply to all aspects and embodiments of this invention.

In a first aspect, the present invention provides a method of screening for, or identifying, host miRNA molecules which modulate viral propagation and/or replication, said method comprising the steps of:

(a) introducing a host cell miRNA modulating compound into a host cell;

(b) contacting the host cell with one or more viruses under conditions to permit infection of the cell with said virus(es);

(c) identifying any modulation of viral propagation and/or replication in said host cell;

wherein modulated viral propagation and/or replication indicates that the host cell miRNA modulating compound modulates a host cell miRNA which may modulate viral propagation and/or replication.

Where step (b) involves contacting host cells with two or more viruses of different species, it may be possible to identify host miRNA molecules which, when modulated, result in multi-species or broad-spectrum, antiviral activity. That is to say, rather than simply inhibiting the propagation and/or replication of a single viral species, modulation of a host cell miRNA identified using the methods described herein, may inhibit the propagation and/or replication of a number of different (i.e. two or more) viral species. It should be understood that the term "multi-species" may encompass two or more different viral species.

Without wishing to be bound by theory, the inventors hypothesise that the host miRNA molecules identified by the method described herein target host cell genes rather than viral genes and as such, viruses are unable to mutate or evolve to escape the effects of modulating these miRNA molecules.

It should be understood that the term "modulation" encompasses both increased and/or decreased (or over- or under-) expression as well as up- or down-regulation events. Furthermore, the term "modulation" covers any increase and/or decrease in function and/or activity. For example, "host cell miRNA modulating compounds" may be compounds which increase and/or decrease the expression, function and/or activity of certain host cell miRNA molecules. In other embodiments, compounds which modulate the activity and/or function of a host cell miRNA molecule, may be those that mimic or inhibit the effect of said host cell miRNA molecules. The phrase "modulation of viral propagation and/or replication" encompasses any increase and/or decrease in levels of viral propagation and/or replication. Similarly, "modulation of host cell miRNA molecules" encompasses increased or decreased expression, function and/or activity of host cell miRNA molecules.

Modulation of host miRNA molecules and/or viral propagation/replication, may be detected relative to the levels of host cell miRNA molecule expression or viral propagation and/or replication occurring in cells into which host cell miRNA modulating compounds have not been introduced. Additionally or alternatively, a control molecule may be introduced into the cell instead of host cell miRNA modulating compounds. Control molecules may take the form of molecules which do not mimic or inhibit host cell miRNA molecules.

Where the methods provided by the first aspect of this invention do not involve the introduction of host cell miRNA modulating compounds or utilise control molecules, these methods may be referred to as reference, standard or control methods. In all cases, the results obtained from the methods provided by the first aspect of this invention may be compared to the results obtained from reference, standard or control methods. Other control, reference or standard methods may lack the step of contacting cells with one or more viruses (step (b)).

One of skill in this field will be familiar with the term "miRNA" which encompasses single-stranded RNA molecules which regulate gene expression. miRNA molecules may be between 10 and 50 nucleotides in length, preferably 15-40, more preferably 16-30 and even more preferably 17-25 nucleotides in length. Typically, miRNA molecules may be between 19 and 26 nucleotides in length. Further information concerning miRNA molecules may be found in, Lagos-Quintana, M., R. Rauhut, W. Lendeckel, and T. Tuschl. "The *C. elegans* heterochronic gene lin-4 encodes small RNAs with antisense complementarity to lin-14". *Cell* 75 (5): 843-54.

In the context of this invention the terms "virus", "viruses" or "viral" are intended to encompass all types of viruses including, for example, DNA and/or RNA viruses. As such, the methods provided by this invention may identify host miRNA molecules which, when modulated, inhibit the propagation and/or replication of a variety of different viruses of different species. In other words modulation of host cell miRNA identified by the methods provided by the first aspect of this invention may result in multi-species or broad spectrum antiviral activity—i.e. antiviral activity which is not specific to just one viral species but to many (i.e. two or more) viral species.

Cells may be contacted with one or more viruses selected from the group consisting of murine cytomegalovirus (MCMV), mouse gammaherpese virus, herpes simplex virus—type I, Semliki-forest virus and human cytomegalovirus (HCMV). One of skill in this field will understand the number of viruses which may be used, (DNA and/or RNA), is large and that the exact choice, may depend on the particular type of cell used.

The steps involved in introducing a host cell miRNA modulating compound into a cell are well known and may involve, for example, the use of transfection protocols or vectors (for example eukaryotic gene expression vectors) such as transcription cassettes, plasmids or viral vectors.

Typically, transfection protocols, including reverse transfection protocols, utilise conditions rendering cell membranes permeable to compounds such as nucleic acids. By way of example, it may be possible to transfect (or reverse transfect) host miRNA mimic and/or inhibitor molecules into cells using electroporation, heat shock and/or compounds such as calcium phosphate or lipid-based reagents.

Additionally, or alternatively, the host miRNA modulating compound may be introduced into the cell by means of a gene gun. In such cases, the nucleic acid to be introduced may be associated with or otherwise conjugated to a particle which can be delivered directly to the cell.

In one embodiment, the host miRNA modulating compound may be introduced into a host cell in the form of a vector. This is particularly useful where the host cell modulating compound takes the form of a nucleic acid (RNA or DNA) molecule. In this case, the term "vector" may encompass plasmids, viral genomes, or other forms of expression cassette suitable for introducing nucleic acid sequences to a cell. Further information on suitable vectors may be found in Sambrook J., Fritsch E., Maniatis T., Molecular cloning: a laboratory manual, Cold Harbor Spring Laboratory Press, second edition, 1989.

The term "host cell" encompasses cells capable of supporting viral replication and as such includes mammalian, such as for example, rodent (mouse, rat, rabbit, guinea pig and the like) or human cells. Plant and/or insect cells are also to be considered as "host cells". In this regard, it is to be understood that any type of mammalian, plant or insect cell may be suitable for use in these methods. In particular, human cells such as fibroblasts, for example MRC-5 fibroblasts may be useful. In other embodiments, murine cells such as, for example, NIH-3T3 cells may be used. Again, it should be understood that the particular choice of cell may influence the choice of virus(es) to be contacted with the cell. For example, where the cell is a human cell, step (b) will likely utilise viral species capable of infecting and propagating/replicating in human cells. Similarly, if the cell is a plant or insect cell, the choice of viral species will likely include species capable of infecting and propagating/replicating in plant or insect cells.

Host cell miRNA modulating compounds may replicate or mimic the sequence of a host cell miRNA molecule—such compounds are referred to hereinafter as "mimic" miRNA molecules. Mimic miRNA molecules may be exploited as a means of increasing or upregulating the expression, activity and/or function of a particular host cell miRNA. By way of example, the cell may be contacted or (reverse) transfected with an miRNA molecule which mimics a host cell miRNA to be up-regulated or over-expressed. In this way, the normal miRNA expression profile of the host cell is supplemented with the mimic miRNA molecule. In one embodiment, the mimic miRNA molecules comprise nucleic acid (DNA or RNA) and may themselves be miRNA molecules.

In other embodiments, the host cell miRNA modulating compounds may inhibit or down-regulate the expression of a particular host cell miRNA. Such compounds may comprise nucleic acid for example, oligonucleotide sequences, specifically designed to inhibit the expression of one or more host cell miRNA sequences—compounds of this type will be referred to hereinafter as "inhibitor compounds". Suitable inhibitor compounds may include, for example, DNA or RNA oligonucleotides, preferably antisense oligonucleotides. Such siRNA oligonucleotides may take the form of single or double-stranded RNA molecules which have been modified in some way (for example by chemical modification) to be nuclease resistant. In order to decrease or down-regulate the expression of a particular host cell miRNA, or to block the activity of the host cell microRNA, the host cell may be contacted or tansfected with any of the abovementioned inhibitor compounds. By analysing native or wild-type host cell miRNA sequences—such as, for example, those described herein as SEQ ID NOS: 22-26, and with the aid of algorithms such as BIOPREDsi, one of skill in the art could easily determine or computationally predict nucleic acid sequences that have an optimal knockdown effect for these genes. Accordingly, the skilled man may generate and test an array or library of different oligonucleotides to determine whether or not they are capable of modulating the expression, function and/or activity of certain host cell miRNA molecules.

To identify any modulation of viral replication and/or propagation it may possible to modify the viruses to include some form of reporter element. For example, the viruses may be modified to include a fluorescent or luciferase reporter moiety. Where two or more viruses are to be added to a cell, each virus may be modified to include different reporter moieties. The expression of such moieties may easily be detected using, for example, optical plate readers and the like. In other embodiments, plaque, complement, antibody, haemolytic and/or haemagglutination assays may be used to detected modulation of viral propagation and/or replication in a host cell. In all cases the amount or number of fluorescent or luciferase moiety, plaques, hamolysis, cell lysis and/or haemagglutination detected, correlates with modulated viral propagation and/or replication.

As stated, modulated viral propagation and/or replication may easily be detected by comparing the results obtained from the method provided by the first aspect of this invention with the results obtained from control, standard or reference method in which no host cell miRNA modulating compound has been introduced. In one embodiment, 0.1-3× increases or decreases in the levels of propogation and/or replication relative to the level of viral propagation and/or replication observed in a control, standard or reference method, may be taken to indicate modulated viral propagation and/or replication. Typically 1.5× increases or decreases in the levels of propogation and/or replication relative to the level of viral propagation and/or replication observed in a control, standard or reference method, may be taken to indicate modulated viral propagation and/or replication.

In a further aspect, the present invention provides a means of testing potential antiviral compounds or drugs. For example, miRNA modulating compounds may be tested to determine whether or not they can be used as antivirals. Such experiments may be conducted in cell based systems, for example in vitro, or in vivo, for example in animals such as rodents. By way of example, a host cell miRNA modulating compound (for example a miRNA mimic or inhibitor compound) may be introduced into a cell or into an animal. Thereafter, the host cell or animal may be contacted with one or more viruses and any modulation of viral propogation and/or replication may be detected as described above. Those miRNA modulating compounds identified as inhibiting viral propogation and/or replication may be used in methods, as compounds or in the manufacture of medicaments for treating viral infections and/or diseases and/or conditions. Host miRNA sequences are often conserved and miRNA compounds which modulate viral propagation and/or replication in, for example, murine systems (including live mice or the like) may be further tested in human systems (for example in human cell lines) and with human viruses. In certain embodiments, cholesterol modified or conjugated miRNA compounds may be tested using these methods. Furthermore, organs such as the liver, spleen, heart, lungs and kidney may be investigated for signs of modulated viral propagation and/or replication. Animals may be administered test antiviral compounds by any suitable route including injection, inhalation (for example via nasal inhalation) or topically.

In addition to providing methods of identifying host cell miRNA molecules which may be modulated as a means of modulating (for example inhibiting) viral propagation and/or replication, the present invention provides specific host cell miRNA molecules which may be targeted for modulation to inhibit viral propagation and/or replication in host cells. These host cell miRNA molecules may be identified by the methods described in the first aspect of this invention. It should be understood that host cell miRNAs may have sequences which are highly conserved across a number of different species. As such, human homologues or orthologues of miRNA molecules identified in other animals, for example rodents etc, may exist. Using the sequence of the miRNA molecules identified in cells of certain animal species, it may be possible to probe for identical or homologous sequences in, for example human cells. Homologous sequences may possess conserved seed sites.

A number of exemplary host miRNA molecules are listed below and have been designated SEQ ID NOS: 1-26 respectively. It should be noted that each the miRNA molecules provided by SEQ ID NOS: 1-26 is conserved between mouse and human cells.

Mir-16
UAGCAGCACGUAAAUAUUGGCG (SEQ ID NO: 1)

Mir-30a-3p
CUUUCAGUCGGAUGUUUGCAGC (SEQ ID NO: 2)

Mir-28
AAGGAGCUCACAGUCUAUUGAG (SEQ ID NO: 3)

Mir-128a
UCACAGUGAACCGGUCUCUUU (SEQ ID NO: 4)

Mir-129-5p
CUUUUUGCGGUCUGGGCUUGC (SEQ ID NO: 5)

Mir-345
GCUGACCCCUAGUCCAGUGCUU (SEQ ID NO: 6)

Mir-222
AGCUACAUCUGGCUACUGGGU (SEQ ID NO: 7)

Mir-223
UGUCAGUUUGUCAAAUACCCCA (SEQ ID NO: 8)

Mir-155
UUAAUGCUAAUUGUGAUAGGGGU (SEQ ID NO: 9)

Mir-27b
UUCACAGUGGCUAAGUUCUGC (SEQ ID NO: 10)

Mir-103
AGCAGCAUUGUACAGGGCUAUGA (SEQ ID NO: 11)

Mir-346
UGUCUGCCCGAGUGCCUGCCUCU (SEQ ID NO: 12)

Mir-542-5p
(C)UCGGGGAUCAUCAUGUCA (SEQ ID NO: 13)

Mir-199a*
UACAGUAGUCUGCACAUUGG (SEQ ID NO: 14)

Mir-24a
UGGCUCAGUUCAGCAGGAAC (SEQ ID NO: 15)

Mir-124a
UAAGGCACGCGGUGAAUGC (SEQ ID NO: 16)

Mir-34b
UAGGCAGUGUAAUUAGCUGAU (SEQ ID NO: 17)

Mir-452
UGUUUGCAGAGGAAACUGAG (SEQ ID NO: 18)

Mir-214
ACAGCAGGCACAGACAGGCAGU (SEQ ID NO: 19)

Mir-107
AGCAGCAUUGUACAGGGCUAUCA (SEQ ID NO: 20)

Mir-744
UGCGGGGCUAGGGCUAACAGCA (SEQ ID NO: 21)

Mir-30a-5p
UGUAAACAUCCUCGACUGGA (SEQ ID NO: 22)

Mir-30b
UGUAAACAUCCUACACUCAG (SEQ ID NO: 23)

Mir-30c
UGUAAACAUCCUACACUCUCA (SEQ ID NO: 24)

Mir-30d
UGUAAACAUCCCCGACUGGA (SEQ ID NO: 25)

Mir-30e
UGUAAACAUCCUUGACUGG (SEQ ID NO: 26)

By over-expressing, up-regulating or mimicking the miRNA molecules provided by SEQ ID NOS: 1-21, or inhibiting the miRNA molecules provided by SEQ ID NOS: 22-26, it is possible to inhibit viral propagation and/or replication in host cells.

It should be understood that unlike miRNA molecules which specifically target the propagation and/or replication cycles of single viral species only, the miRNA molecules listed as SEQ ID NOS: 1-26 target host genes, cell systems and/or pathways and, when their expression is modulated, display multi-species (or broad spectrum) antiviral activity. That is to say, each of the miRNA molecules provided herein are effective in inhibiting the propagation and/or replication of a variety of viral species (i.e. two or more species) in host cells.

In one embodiment, the specific host cell miRNA molecules which may be targeted for modulation in order to inhibit host cell viral propagation and/or replication are not host cell miRNA molecules modulated by a virus and/or not modulated in all cell types/tissues at all stages in the life cycle of a virus. In otherwords, the compounds provided by this invention may not target host cell miRNA molecules which are up or down regulated in response to a viral infection. For example the miRNA molecules known as Mir-17/92, Mir-28, Mir-93, Mir-100, Mir-101, Mir-122, Mir-125b, Mir-130b, Mir-146, Mir-150, Mir-155, Mir-203, Mir-218, Mir-223 and Mir-382 may be excluded from the scope of this invention.

Accordingly, a second aspect of this invention provides a multi-species antiviral compound capable of modulating the expression, function and/or activity of one or more host cell miRNA molecules, for treating viral infections, diseases and/or conditions.

A third aspect of this invention provides a multi-species antiviral compound capable of modulating the expression, function and/or activity of one or more host cell miRNA molecules for the manufacture of a medicament for treating viral infections, diseases and/or conditions.

A fourth aspect of this invention provides a method of treating a subject suffering from a viral infection, disease and/or condition, said method comprising the steps of administering a pharmaceutically effective amount of a multi-species antiviral compound capable of modulating the expression of one or more host cell miRNA molecules.

In one embodiment the one or more host cell miRNA molecules are those provided by SEQ ID NOS: 1-26 above.

One of skill will appreciate that the compounds capable of modulating host cell miRNA molecules mentioned in the second, third and fourth aspects of this invention might take the form of the miRNA mimic or inhibitor compounds described above.

As far as the miRNA molecules identified as SEQ ID NOS: 1-21 are concerned, compounds comprising these sequences may be used to mimic or over-express the corresponding miRNA molecules in host cells. Accordingly, a further aspect of this invention provides (a) multi-species antiviral compounds selected from the group consisting of SEQ ID NOS: 1-21 for use in treating viral infections; (b) the use of multi-species antiviral compounds selected from the group consisting of SEQ ID NOS:1-21 for the manufacture of a medicament for treating viral infections; and (c) a method of treating viral infections, said method comprising the steps of administering a pharmaceutically effective amount of a composition comprising multi-species antiviral compounds selected from the group consisting of SEQ ID NOS: 1-21.

It should be understood that the compositions, medicaments and methods provided by this invention may comprise or use one or more of the sequences provided as SEQ ID NOS: 1-21 above. For example, a composition or medicament for treating a viral infection may comprise two or more of the miRNA sequences described herein. Compositions, medicaments and methods which pool or combine compounds selected from those consisting of SEQ ID NOS: 1-21, may be particularly useful when treating patients infected with two or more viruses of different species. Furthermore, the compositions, medicaments and/or methods described herein may be combined with any number of existing antiviral compounds or treatments.

In one embodiment, the miRNA molecules provided by this invention may comprise the seed sequence of a miRNA molecule identified as being potentially useful for treating viral infections and/or diseases and/or conditions caused or contributed to by one or more viral species. For example, a seed sequence may comprise the first 1-8 or 2-7 nucleotides of the 5' end of a miRNA molecule, including those listed above as SEQ ID NOS 1-26. One of skill in this field will appreciate that since the seed sequence is generally the functional part of a miRNA molecule, the remainder of the miRNA sequence may be highly variable. In particular, one embodiment of this invention relates to miRNA molecules comprising the seed sequences of the miRNA sequences designated SEQ ID NOS: 10, 11 and 20 above.

In a sixth aspect, the present invention provides pharmaceutical compositions comprising any of the compounds described above (for example, the host cell miRNA modulating (mimic and/or inhibitor) compounds including SEQ ID NOS: 1-26), in association with a pharmaceutically acceptable excipient, carrier or diluent. Such compositions may find application in, for example, the treatment of viral infections and/or diseases and/or conditions caused or contributed to by, viruses.

Preferably, the pharmaceutical compositions provided by this invention are formulated as sterile pharmaceutical compositions. Suitable excipients, carriers or diluents may include, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycon, sodium carboxymethylcellulose, polyacrylates, waxes, polyethylene-polypropylene-block polymers, polyethylene glycol and wool fat and the like, or combinations thereof.

Said pharmaceutical formulation may be formulated, for example, in a form suitable for oral, parenteral or topical administration. Pharmaceutical compositions formulated for topical administration may be presented as an ointment, solution or a suspension in an aqueous or non-aqueous liquid, or as an oil-in-water liquid emulsion.

One of skill will appreciate that the host cell miRNA modulating compounds provided by this invention may be formulated for administration in a variety of different ways. For example, the host cell miRNA modulating compounds provided by this invention (for example those detailed as SEQ ID NOS: 1-21) may be provided in the form of a vector for introduction and expression in a cell.

In addition to the above, the present invention provides a means of identifying host genes, cell systems or pathways (for example innate immune pathways involving for example Tol receptors, Tol-Like receptors and the like) which may be targets for antiviral therapy. For example, by using the methods described in the first aspect of the invention to identify host cell miRNA molecules which may be modulated to inhibit viral propagation and/or replication, it may be possible to identify the specific genes, cell systems and/or pathways targeted by the host cell miRNA. Identification of the genes, cell systems and/or pathways associated with, or modulated by the host cell miRNA molecules identified by a method according to the first aspect of this invention, may provide further targets for antiviral therapies. By way of example, the inventors have determined that genes modulated by mir-30, include those listed below:

(1) ankyrin repeat, family A (RFXANK-like), 2
(2) isocitrate dehydrogenase 1 (NADP+), soluble
(3) kelch-like 20 (*Drosophila*)
(4) LIM homeobox protein 8
(5) transcription factor Dp 1
(6) collagen triple helix repeat containing 1
(7) glucosamine-6-phosphate deaminase 1
(8) dpy-19-like 1 (*C. elegans*)
(9) neuron specific gene family member 1
(10) transmembrane protein with EGF-like and two follistatin-like domains 1
(11) twinfilin, actin-binding protein, homolog 1 (*Drosophila*)
(12) PRKC, apoptosis, WT1, regulator
(13) SET domain containing (lysine methyltransferase) 7
(14) cDNA sequence BC031353
(15) like-glycosyltransferase
(16) LIM and calponin homology domains 1
(17) scavenger receptor class A, member 5 (putative)
(18) unc-5 homolog C (*C. elegans*)
(19) zinc finger, DHHC domain containing 17
(20) c-abl oncogene 1, receptor tyrosine kinase
(21) phosphatidylinositol transfer protein, membrane-associated 2
(22) retinoic acid receptor, gamma
(23) LIM homeobox protein 9
(24) N-acetylglucosamine-1-phosphodiester alpha-N-acetylglucosaminidase
(25) procollagen-proline, 2-oxoglutarate 4-dioxygenase (proline 4-hydroxylase), alpha II polypeptide
(26) sarcoglycan, beta (dystrophin-associated glycoprotein)
(27) SNAP-associated protein

(28) UDP-Gal:betaGlcNAc beta 1,4-galactosyltransferase, polypeptide 6
(29) dapper homolog 1, antagonist of beta-catenin (*xenopus*)
(30) phosphatidylinositol-5-phosphate 4-kinase, type II, alpha
(31) protein tyrosine phosphatase, non-receptor type 13
(32) ring finger protein 122
(33) sodium channel, voltage-gated, type II, alpha 1
(34) WD repeat domain 7

In addition, the genes/pathways regulated by miR-199a are detailed in FIG. 16.

In view of the above, it is apparent that ephrin receptor signalling, thrombin signalling, inositol phosphate metabolism and cytoskeleton organisation are important pathways modulating broad pro- or anti-viral cellular processes.

One of skill will appreciate that while the present invention has been described with reference to viral infections, diseases and or conditions, the methods, medicaments and compositions described herein may also find application in the treatment of infections diseases and/or conditions caused or contributed to by other pathogens. For example, the scope of this invention may extend to the treatment of bacterial (particularly intracellular bacterial) infections and/or parasitic infection including those caused or contributed to by protozoan parasites (for example Trypanosomes and the like). In addition, the present invention may provide methods of screening for, or identifying, host miRNA molecules which may be modulated to inhibit the replication, propagation and/or intracellular entry of other pathogens such as bacterial and/or protozoan pathogens.

BRIEF DESCRIPTION OF THE DRAWINGS

The present invention will now be described in more detail with reference to the following Figures which show:

(FIG. 1A) Overview of screening protocol: miRNA mimics or inhibitors were reverse transfected into NIH-3T3 cells (6 technical replicates) and incubated for 60 hrs prior to cell viability analysis (n=3) or infection with GFP virus (n=3). (FIG. 1B) Fluorescent growth curve of GFP-reporter viruses in NIH-3T3 cells; Y1 axis shows values for MCMV and MHV-68 and Y2 shows values for HSV-1; error bars depict standard deviation of 3 technical replicates. White lines indicate time points used for subsequent analysis. (FIG. 1C) Normalized fluorescence data (at 70 hours post infection, hpi, for MCMV and 57 hpi for MHV-68 and HSV-2). Negative controls (RISC-free siRNA, *C. elegans* miR—mimic or *C. elegans* miR—inhibitor) have <10% effect on GFP signal compared to >50% knock-down using siRNA targeting GFP (n=3, error bars depict standard deviation).

(FIG. 11A) Infected cells were visualized 24 hours post-infection. (FIG. 11B). RNA was harvested from cells transfected with mimic or inhibitor for 48 hours and RT-PCR performed to quantify (relative) expression of mir-30d under these conditions, as well as the other mir-30 family member (mir-30) or a control host microRNA (mir-16) that shouldn't be effected by the transfection. This shows over-expression (~40 fold) of mir-30d by mimic and inhibition (~85%) by inhibitor.

(FIG. 12A) Changes in miRNA expression in response to MCMV or HCMV. Northern blot analysis of total RNA isolated from mouse fibroblast NIH-3T3 cells infected with MCMV at MOI=3 (harvested 24 hrs post infection) or human fibroblast MRC-5 cells infected with HCMV at MOI=3 (harvested 48 hours post infection). (FIG. 12B) Examination of anti- or pro-viral effects of miRNAs on Semliki forest virus using a replicon expressing renilla. In all experiments n=4 and error bars indicate standard deviation.

DETAILED DESCRIPTION

Figure 1A:
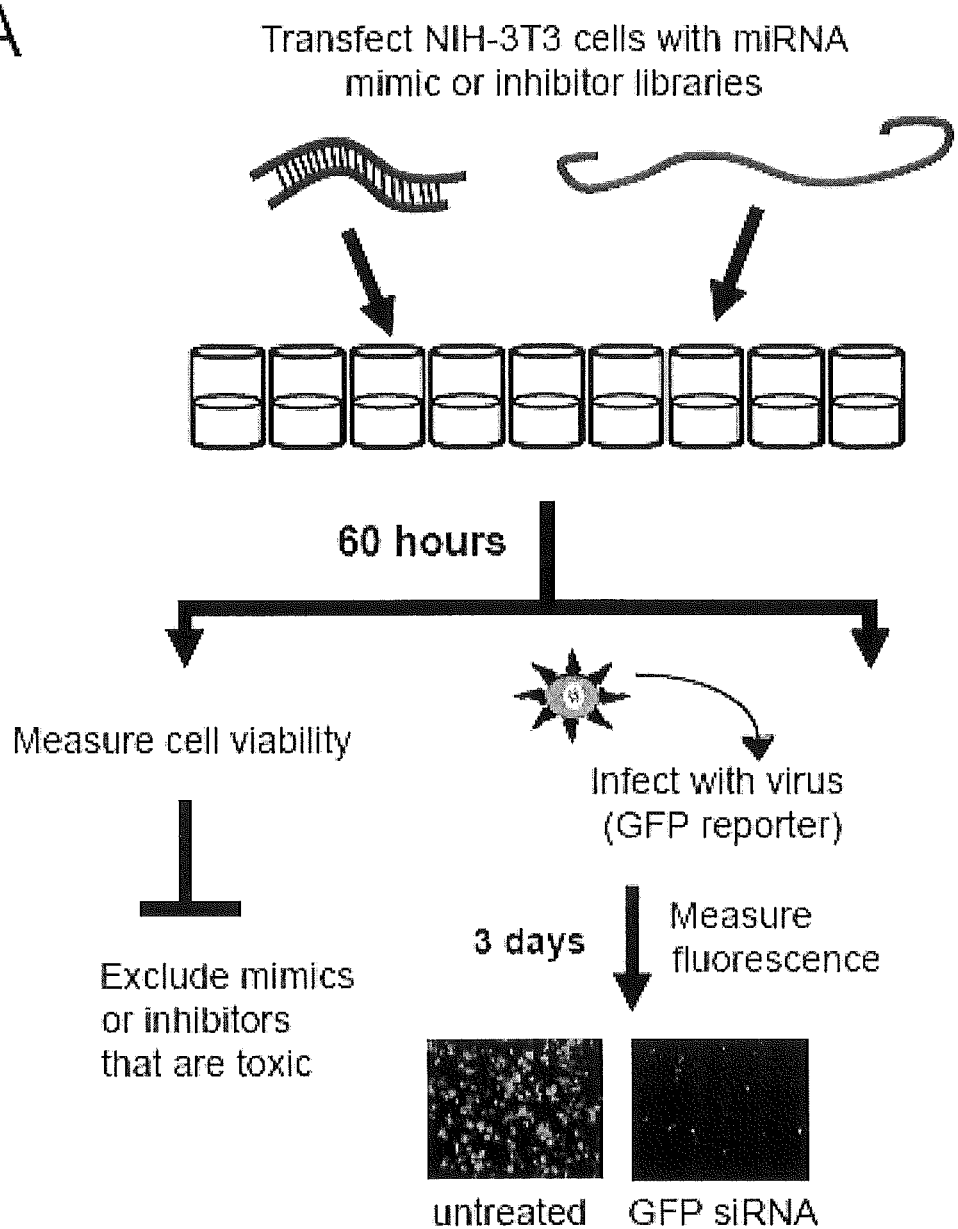
FIGS. 1A-1C: Agonist-antagonist miRNA screening.

Materials & Methods
Cells & Viruses

The viruses used in this study are described elsewhere. Briefly, mcmv-gfp encodes a gfp expression cassette in front of the mcmv ie2 gene [1], a gene that is under immediate early control and is non-essential for growth in tissue culture [2]. Wild-type and mcmv-gfp viruses were propagated in NIH-3T3s and titred in p53 MEFs as described elsewhere [3]. The MHV-gfp virus is officially termed "LHAgfp", and contains an insertion cassette inserted in the 5' end of the genome that encodes gfp driven by the human cytomegalovirus immediate early promoter. This cassette replaces nt 1-3223, which encodes viral factors m1 and vtRNAs (the deletion of which does not significantly alter viral growth kinetics in vitro, B. Dutia, unpublished data) [4]. The LHAgfp viral stocks were prepared on BHK-21 cells as described elsewhere [5]. The HSV-gfp27 virus encodes a gfp cassette that replaces the ICP27 gene and is under control of the natural ICP27 promoter [6].

Transfection & Screening Protocol

MicroRNA mimics or inhibitors were reverse transfected into NIH-3T3 cells at a final concentration of 25 nM in 0.4% Dharmafect 1 (transfection reagent), with $1.5 \times 10^4$ cells per 96 well. Lipid was diluted to 4% in 10 uL of serum free media (optimem) for 5 minutes prior to mixing with miRNA mimics; the mimics+ lipid (10 uL+10 uL) were then incubated 20 minutes in serum-free media (optimem) prior to addition of cells (80 uL at $1.875 \times 10^4$/ml) in Dulbecco's modified Eagle's medium (DMEM; Invitrogen) supplemented with 10% calf serum. Transfected cells were then incubated 60 hrs at 37 C, 5% CO2, after which the media was removed and cells were infected with virus at an MOI of 0.2. Viruses used were murine cytomegalovirus (BAC-derived strain with GFP inserted under immediate early control), mouse gammaherpesvirus (BAC-derived strain with GFP reporter) or herpes simplex virus-1 (BAC-derived strain with GFP reporter) or Semliki Forest virus (luciferase reporter) in 2% Calf serum, DMEM media+1% penicillin-streptomycin. Cells were inoculated with the virus for 1 hr at 37 C, 5% CO2, after which virus was removed by flicking the plate, followed by addition of 100 uL phenol-red free DMEM media+1% penicillin-streptomycin. Gas-permeable membranes were then affixed to the plate to prevent evaporation and plates were incubated at 37 C, 5% CO2 for up to 140 hours. The fluorescent signal was measured every in the linear growth time range (50-80 hrs) for MCMV, MGHV, and HSV-1 infected cells using a fluorescent plate reader. For infections with Semliki Forest Virus, luciferase was measured between 2-10 hrs post infection. For validation studies, microRNA mimics or inhibitors were reverse transfected into C127 cells at a final concentration of 25 nM in Lipofectamine 2000 at 0.3% (transfection reagent), with $1.5 \times 10^4$ cells per 96 well, maintained in 10% Calf serum, DMEM media+1% penicillin-streptomycin prior to infectin with MCMV (as above). MicroRNA mimics or inhibitors were reverse transfected into MRC-5 cells at a final concentration of 25 nM in Dharmafect 1 at 0.3% (transfection reagent), with $1.5 \times 10^4$ cells per 96 well. Transfected cells were then incubated 60 hrs at 37 C, 5% CO2, after which the media was removed and cells were infected with human cytomegalovirus (GFP reporter) at an MOI of 0.5. The fluorescent signal was measured in the linear growth range under these conditions (40-70 hr postinfection).

Cell Viability Assays

Following reverse transcription and mock-infection, the effect of mouse miRNAs on cell viability was assessed with Cell titre blue assay (Promega), using a cut-off of 80%. Some miRNA mimics impacted the ability of NIH-3T3 cells to adhere properly during reverse transfection and this could also be identified by cell titre blue (since cells were washed away in the protocol) and confirmed by visual inspection. MiRNAs that were toxic or interfered with adherence to the plates (26 of the 301 examined) were removed from further analysis. miRNA mimics and inhibitors identified as "hits" in the viral assays were re-examined for impact on viability as above.

Data Normalization and Analysis for Screening

For each virus, the miRNA mimic and inhibitor libraries were screened in two independent experiments, each with a minimum of 3 technical replicates.

For normalization, the background signal from uninfected cells was subtracted from the corresponding foreground signal for each well. Data were then transformed to log 2 scale. Variation in fluorescent intensity between individual plates within a given screen was normalised to the median of control wells included on each plate: non-transfected cells, cells transfected with RISC-free siRNA, C. elegans miR-67 mimic and C. elegans miR-67 inhibitor. A positive control for transfection efficiency (gfp siRNA) was included in each screen, requiring knockdown of >50%.

Influenza Virus Plaque Assay

MDCK cells were reverse transfected with 25 nm miR-NAs at 1×10^6 cells per well in a 6 well plate using DharmaFECT 3 at 0.3% (Lipid). 48 hrs post transfection cells were infected with Mouse adapted Influenza virus (A/WSN/33) and incubated for 1 hr. After infection 2 ml of media was added with 2% agarose and 0.1 mg/ml of N-acetyl trypsin. Infected cells were then incubated at 37 c and 5% Co2 for 3 days. Cells were then fixed with 10% neutral buffered formalin for 24 hrs. Plaques were counted after brief staining in 0.1% toluidene blue.

Hep2 Cells/HSV Experiment

Hep2 cells were reverse transfected with 25 nm of miR-NAs at 1.5×10^4 cells/well in a 96 well plate using DharmaFECT 3 at 0.3% (Lipid). 48 hrs post transfection cells were infected with HSV-1 (GFP virus) at moi of 0.5. The fluorescence signal was measured over time.

Pooling Experiments:

The concentration of individual miRNA was adjusted based on the number of miRNAs in a pool so as to make the final concentration of the miRNA pool at 25 nm. miRNA pools were transfected the same way as other individual miRNAs. The reason we chose to examine miR-23,24,27 is that they all come from the same cluster.

Results

Agonist-Antagonist miRNA Screen.

Figure 1B:
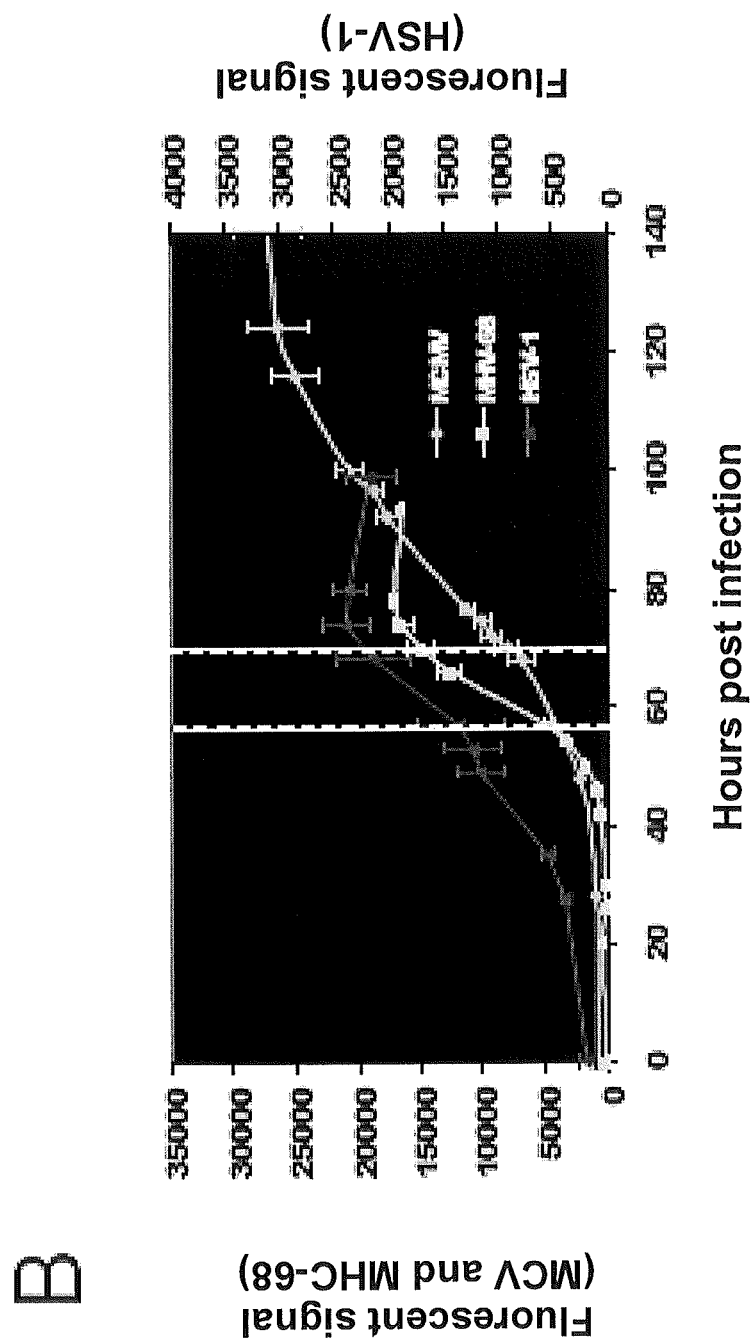
Figure 1C:
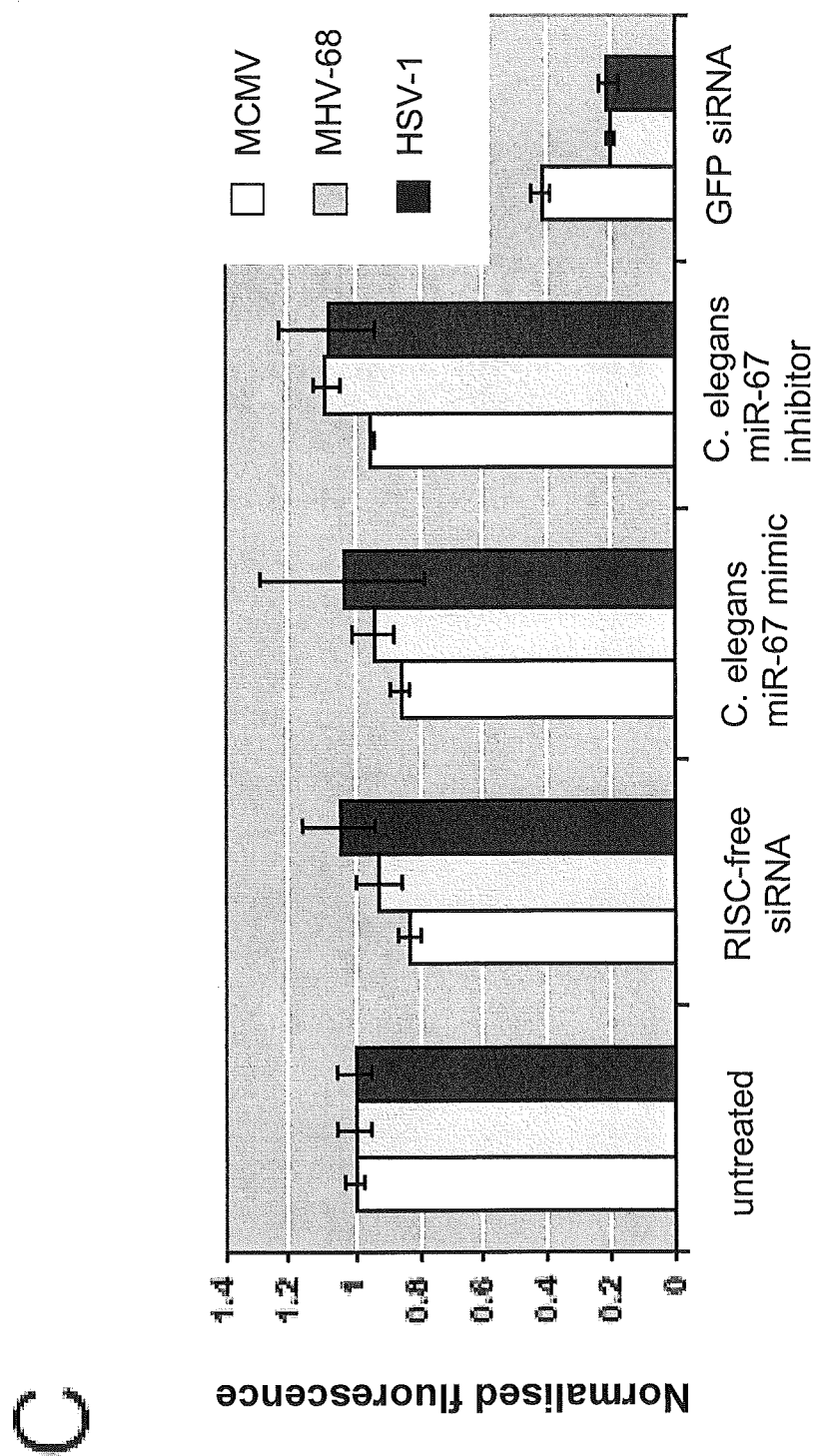

The agonist-antagonist screening protocol reported here involves over-expressing or inhibiting miRNAs by transfection of synthetic mimics or inhibitors, followed by analysis of the impact on viral growth (using viruses encoding GFP reporters; FIG. 1A). Screening was conducted in a murine fibroblast cell line (NIH-3T3) which supports replication of representatives of all three herpesviral families: murine cytomegalovirus (MCMV), mouse gammaherpesvirus (MHV-68) and herpes simplex virus-1 (HSV-1), FIG. 1B. Despite the large evolutionary distance between these viruses is (~200 million years [19]) all three viruses require, manipulate and evade common host cell processes (cell cycle, apoptosis, interferon response) which are expected to be regulated by miRNAs and can be interrogated in vitro. Cells were infected at a low multiplicity of infection (0.2-0.5), such that the fluorescent signal detected by ~60-70 hrs is based on multiple rounds of replication and the impact of a miRNA on any stage of the replication cycle should therefore be detectable. One assumption in this screening approach is that transfection alone does not itself impact viral replication. This is confirmed by transfections using *C. elegans* miRNA mimics or inhibitors or a "RISC-free" siRNA (which gets taken up by cells but not incorporated into RISC). As shown in FIG. 1C, these reagents have less than a 10% effect on the GFP signal, compared to >50% knockdown with a siRNA directed against GFP. Controls were included in each plate to normalize plate-to-plate variation in fluorescent intensity. To account for miRNA mimics or inhibitors that result in general toxicity to the cells, viability assays were performed in parallel. Twenty six miRNA mimics (representing 8% of the library) were excluded from analysis due to toxicity to cells and/or altered adherence properties; none of the inhibitors were scored as toxic.

The Effect of Murine microRNAs on the Growth of Murine Cytomegalovirus, Mouse Gammaherpesvirus and Herpes Simplex Virus-1 in Murine Fibroblast Cells (NIH-3T3).

Figure 2:
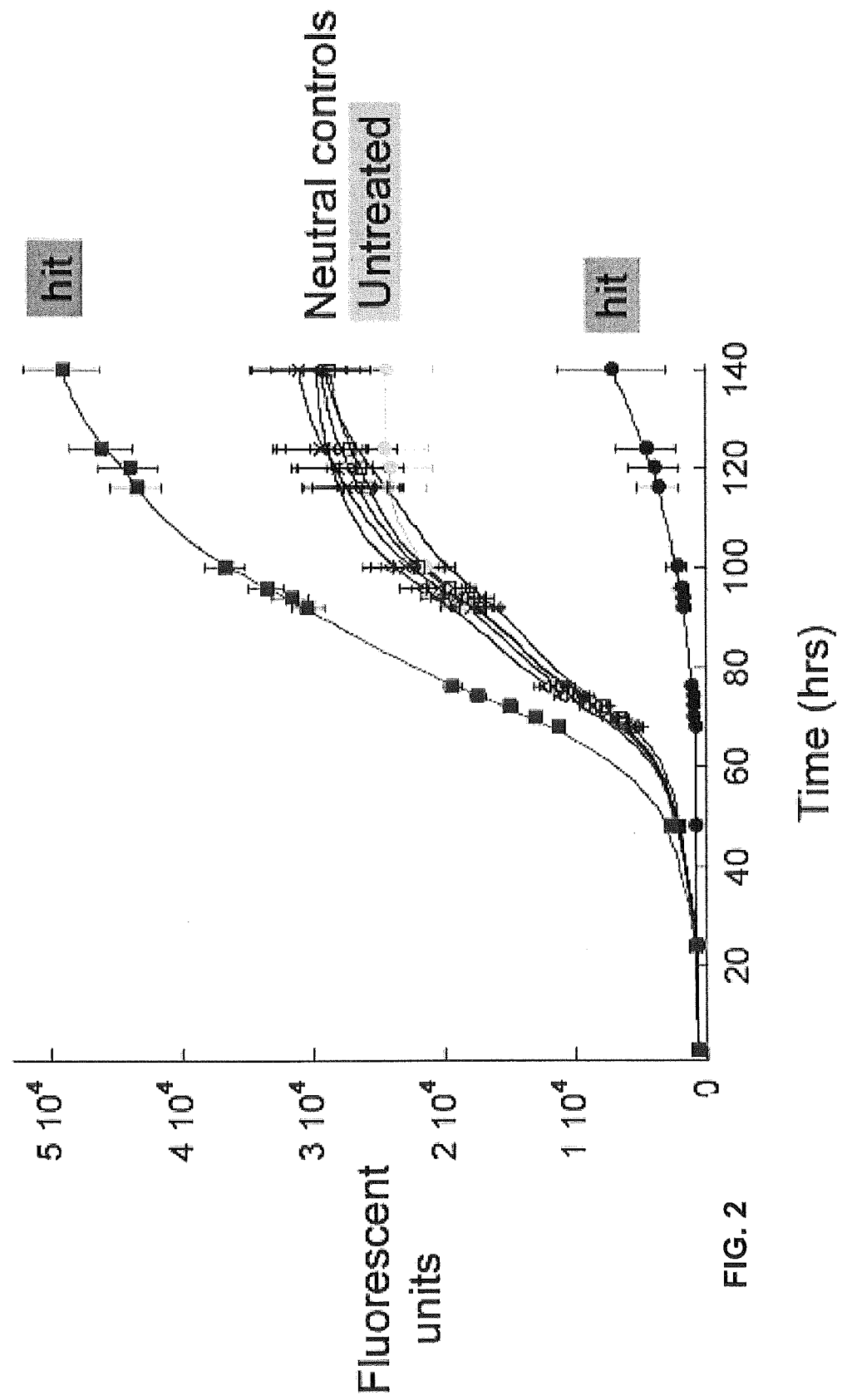
FIG. 2: Viral growth curve of MCMV in NIH-3T3 cells (the virus is engineered to encode a GFP protein used for detection with a polar star plate reader). The GFP signal correlates with viral accumulation in these cells over time. The goal in developing the assay was to be able to examine the effects of over expressing or inhibiting microRNAs on viral replication in a semi-high throughput way. The model is that an "anti-viral" miRNA will inhibit replication when over expressed (compared to a neutral control), and conversely, a miRNA that normally inhibits replication will cause an increase in replication when it is inhibited. The neutral controls used are *C. elegans* microRNAs not encoded by the mouse that should not target mouse genes and are not expected to have an effect on replication. This figure shows two "hits"—one that decreases replication and one that increases replication. Although we take measurement for ~6 days, the standard deviation is higher at longer time points and we therefore analyse the data around ~70 hrs, where the virus is in the linear phase of growth.
Figure 3:
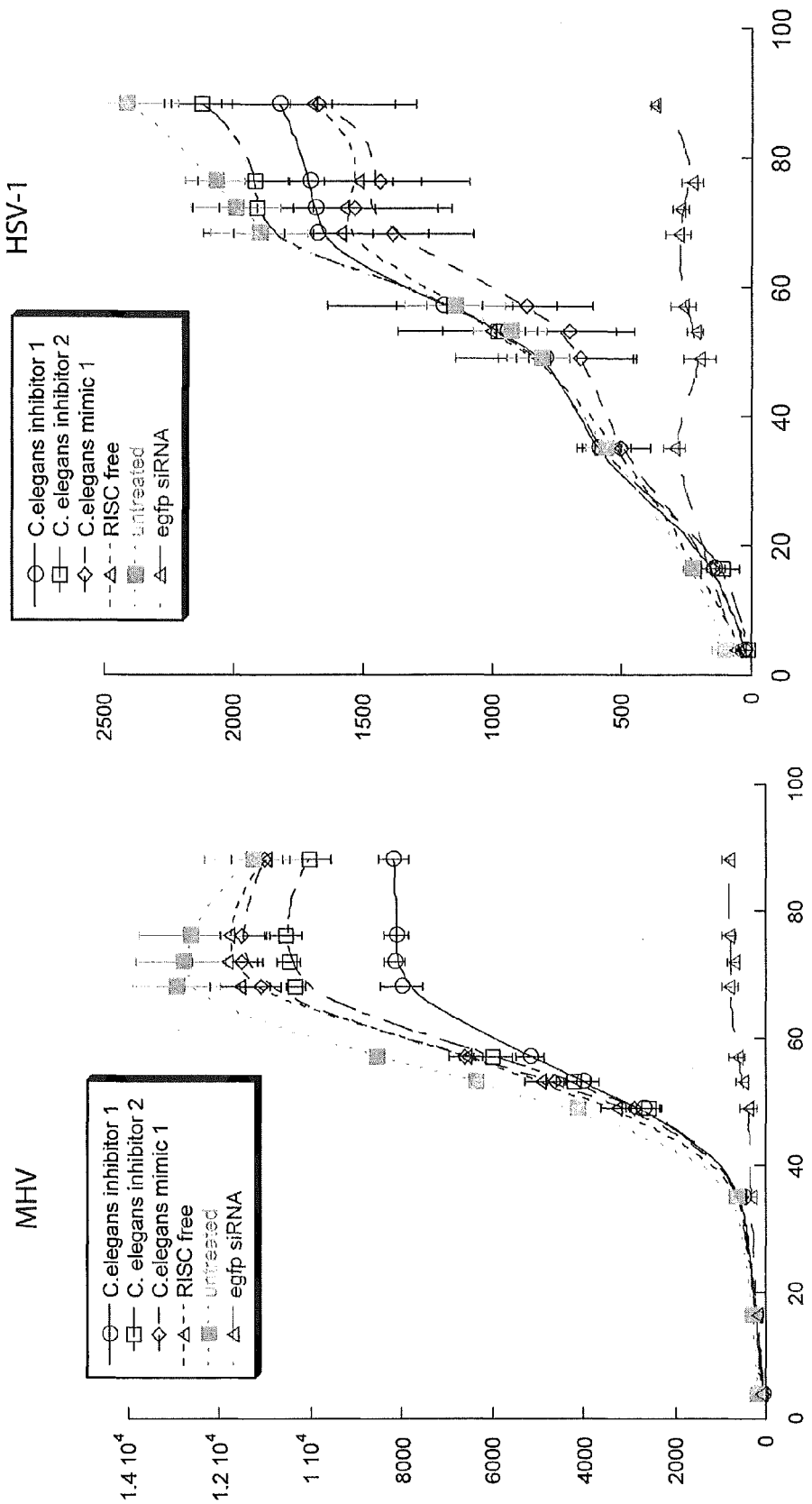
FIG. 3: Example of the growth curves obtained with the other 2 viruses used, MHV and HSV-1. Since the growth kinetics are different than MCMV, we analyze data at 58 hours, where the virus is in the linear phase of growth and the signal to background is high. These curves show the neutral controls and a positive control (siRNA against GFP).

The effect of murine microRNAs on the growth properties of three different viruses; murine cytomegalovirus, mouse gammaherpesvirus and herpes simplex virus-1 was examined in murine fibroblast cells (NIH-3T3), using genome wide miRNA-mimic libraries. FIG. 2 shows the growth curve of MCMV with neutral controls and representative "hits" and FIG. 3 shows the growth curve of MHV and HSV-1 with neutral controls and a positive control (siRNA against the reporter—GFP).

Four miRNAs represent the highest confidence anti-viral microRNAs in all three herpesviral subfamilies (based on a growth defect when the miRNA is over-expressed and increased quantity of virus when the miRNA is inhibited): mir-199a, miR-214, miR-24 and miR-103. Two miRNAs, miR-30b and miR-30d, show the opposite properties (increased growth when over-expressed and decreased growth when inhibited). Combining this work with expression analysis, we demonstrate that mir-199a and miR-214 (which derive from a common cluster) are down-regulated upon infection in both murine and human cytomegalovirus. Expression and network analysis suggests that mir-199a-3p regulates a range of genes involved in the immune response, cellular movement and immune cell trafficking. Pooling experiments further demonstrate that miRNAs which are clustered together (miR-199a-5p, mir-199a-3p and miR-214) can provide additive effects in inhibiting viral growth capacity. Host miRNAs are a tune-able and consequential feature of viral infection and provides the first evidence that these molecules hold broad anti-viral potential against multiple viruses.

Figure 4:
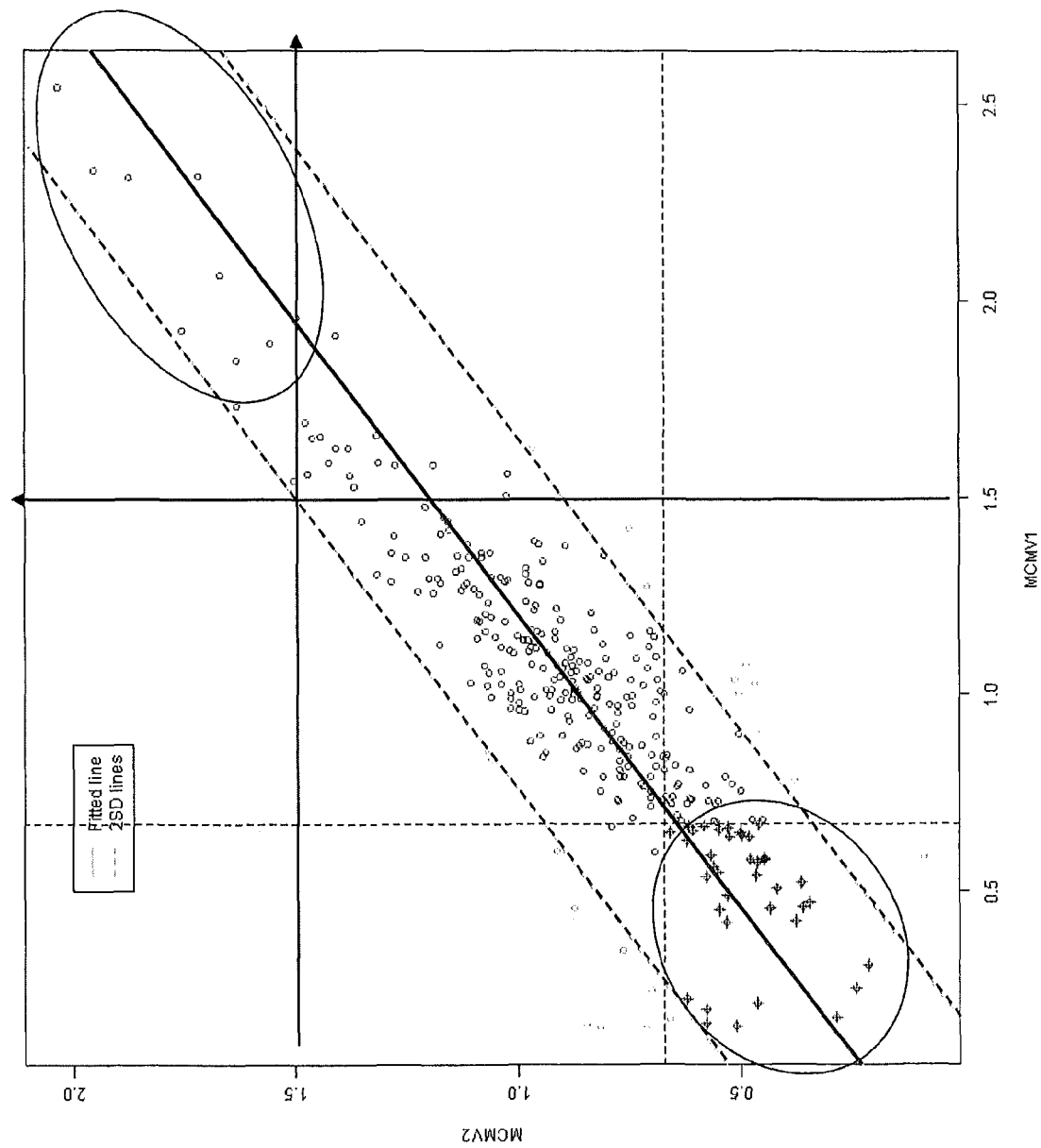
FIG. 4: Shown in opals are hits that have >1.5 or <1.5 effect on replication. The microRNAs in the lower left quadrant are considered candidates for "anti-viral" microRNAs that could be mimicked with synthetic reagents as a therapeutic strategy. One miRNA family, mir-30 (mir-30a-5p, mir-30b, mir-30c, mir-30d, mir-30e) resulted in >1.5× increase in replication compared to controls in all three viruses (data shown for MCMV above, these are in the upper right quadrant).
Figure 5:
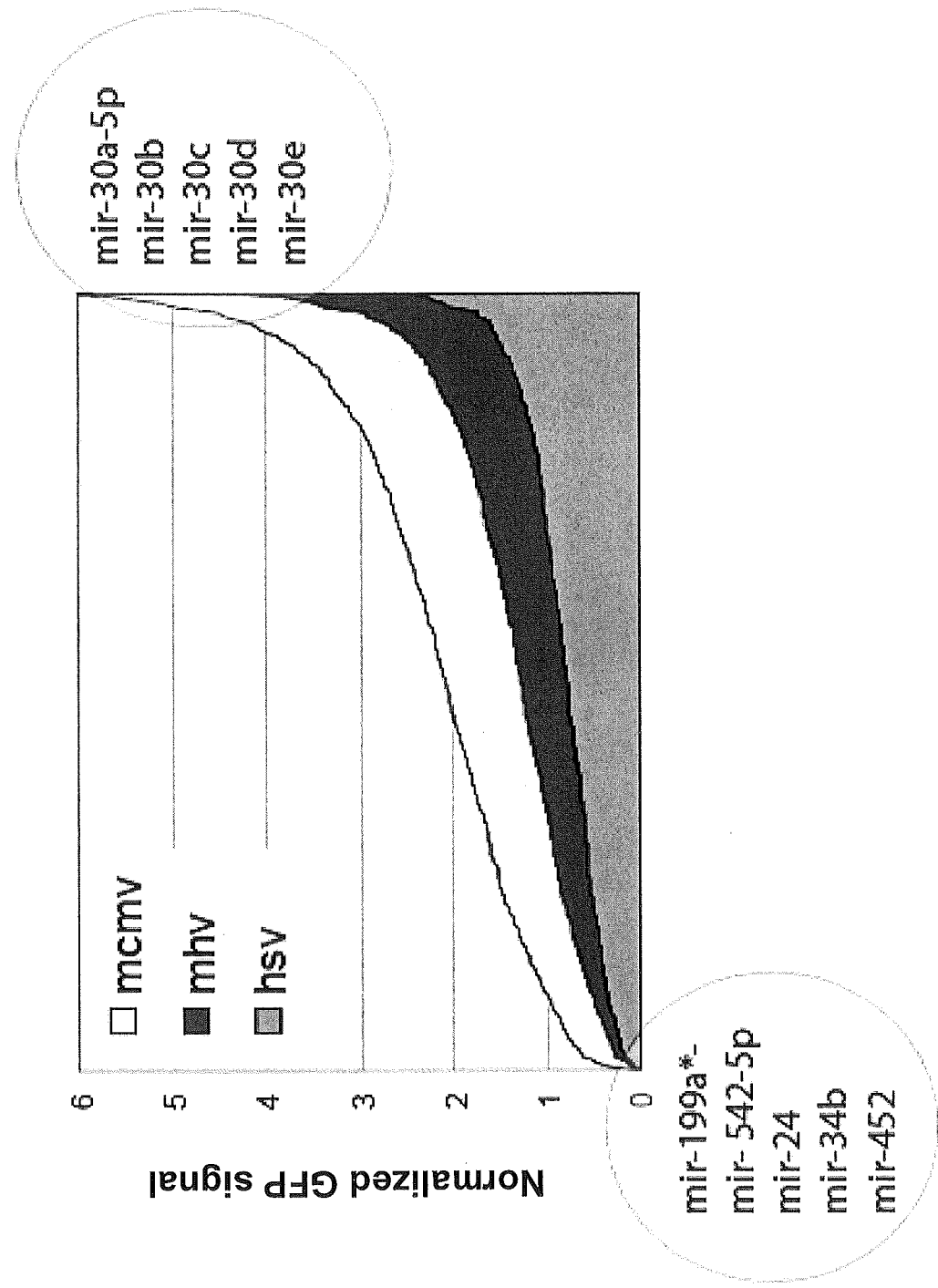
FIG. 5: Shows the GFP signal obtained for all 3 viruses using the mimic libraries (x axis is the different miRNA mimics, y axis is the GFP signal reflecting extent of replication). As is shown, there are several microRNAs that result in decreased replication in all three viruses when over-expressed. There are other microRNAs (mir-30 family) that result in increased replication when over-expressed. We have made the cutoffs as described in FIG. 5.
Figure 6:
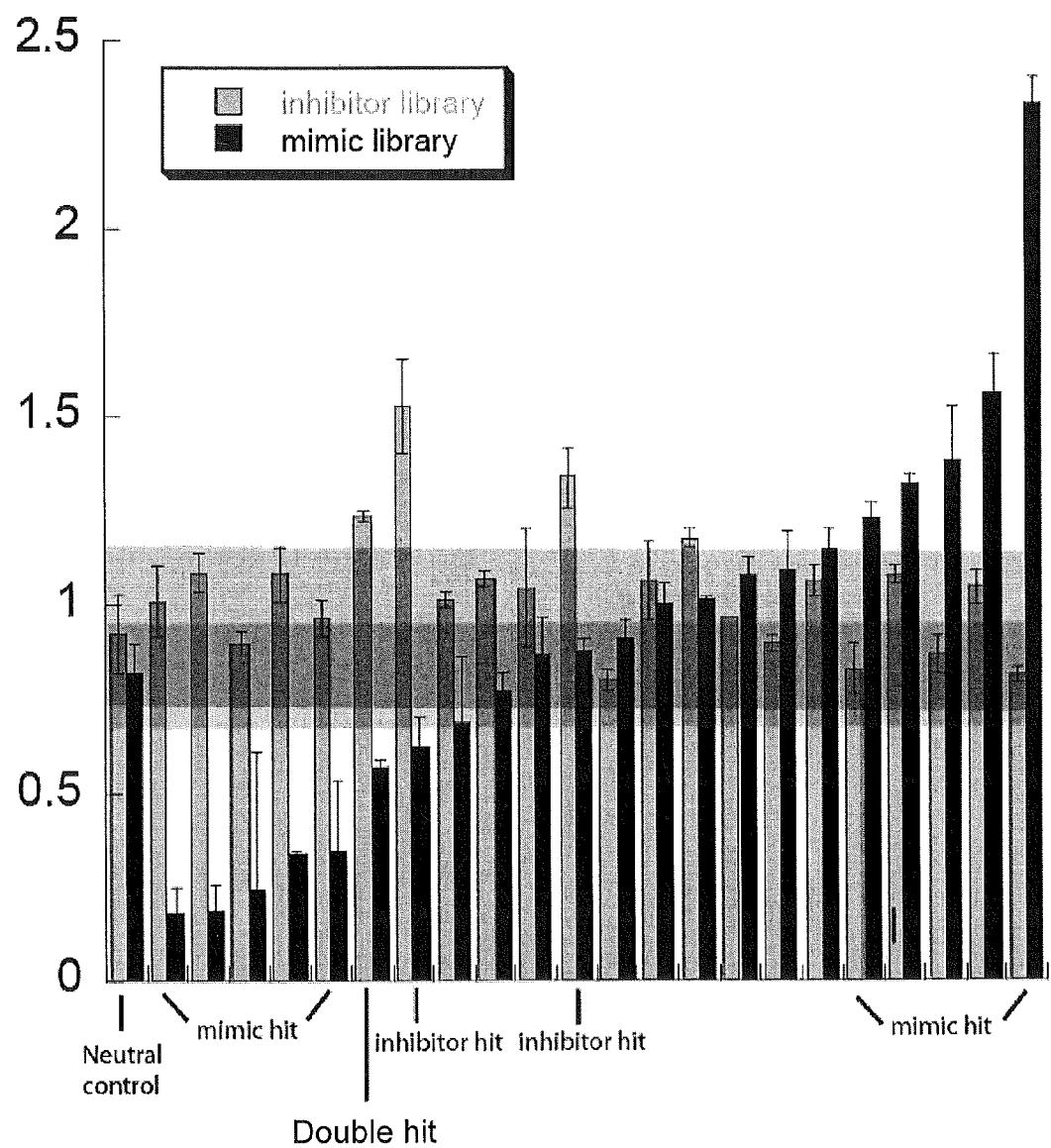
FIG. 6: Shows some of the "hits" in MCMV. In the left column is the normalized fluorescent value of the controls—reflecting the amount of viral replication in cells transfected with the *C. elegans* microRNA mimic (black bars) or inhibitor (gray bars). The shaded boxes show two standard deviations of the controls, so values below or above these boxes are considered to be "hits". As shown, some miRNAs significantly influence replication when they are over-expressed, "mimic hits"—some decrease replication and some increase replication. Other miRNAs significantly influence replication when they are inhibited—"inhibitor hits". It is the "double hits" are miRNAs that decrease replication when they are over-expressed and increase replication when they are inhibited. Having these two corroborating results helps validate/screen the data for REAL hits. These double hits would be miRNAs that could be used as anti-viral drugs (over-expressing miRNAs in vivo to control/treat an infection). However, not all miRNAs are expressed in this cell type, therefore, in the inhibitor screen there could be false negatives (if a miRNA is not expressed then inhibiting it should have no effect). Therefore, we rely primarily on mimic data for identification of the anti-viral microRNA candidates In addition, there are some miRNAs that seem to be "pro-viral", in that replication increases in the presence of the mimic and/or decreases in the presence of the inhibitor. These would be another type of drug target—where inhibiting this microRNA would be a method for controlling the infection.
Figure 8:
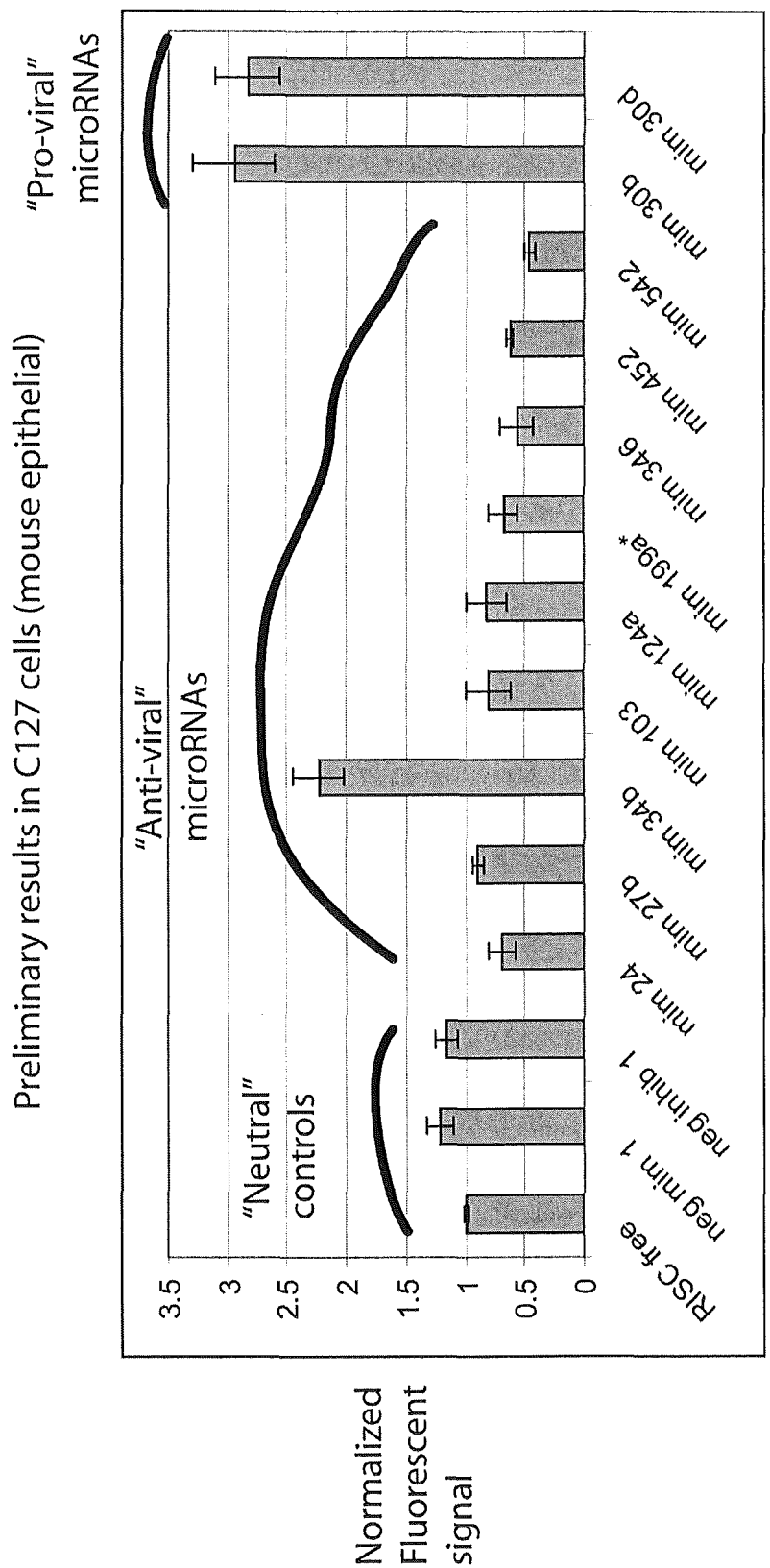
FIG. 8: Initial data with C127 cells and MCMV. Viral growth was measured as described above, but data analyzed at 51 hours based on the faster growth kinetics under these conditions (signal/noise required MOI of 0.5).

To define microRNA hits, the normalized fluorescent values obtained for the screens were plotted with a given virus as shown in FIG. 4. The y axis represents values obtained in one screen (median values based on n=3) and the x axis represents values obtained in another independent screen (FIG. 3 shows the 2 independent MCMV screens). We excluded mimics that fell outside 2 st-deviations (dashed lines) for the 2 screens as these are expected to be outliers. We also excluded from this analysis miRNAs that had toxicity or adhesion effects (removed 26 of the total 301 unique mouse miRNAs), based on cell-titre blue assay and visual inspection of wells. We found a total of 21 miRNAs that resulted in >1.5× decrease on replication in two independent screens with all 3 viruses when transfected into cells prior to infection (listed in Table 1 below)—see FIG. 8; and one family of microRNA, mir-30 which resulted in >1.5× increase on replication in all 3 viruses.

In Vitro Screening Results—Inhibitor Libraries

The results from screening microRNA inhibitors may be used to corroborate results, however, it is important not to use these results to "rule out" any of the hits. This is for 2 reasons: 1) not all of the microRNAs are expressed in the cell type we're using and therefore there are likely to be a number of false negatives for inhibitor results. 2) the anti-viral effect of microRNAs may require them to be expressed at higher than endogenous levels.

Validation in Other Cell Types

Figure 7:
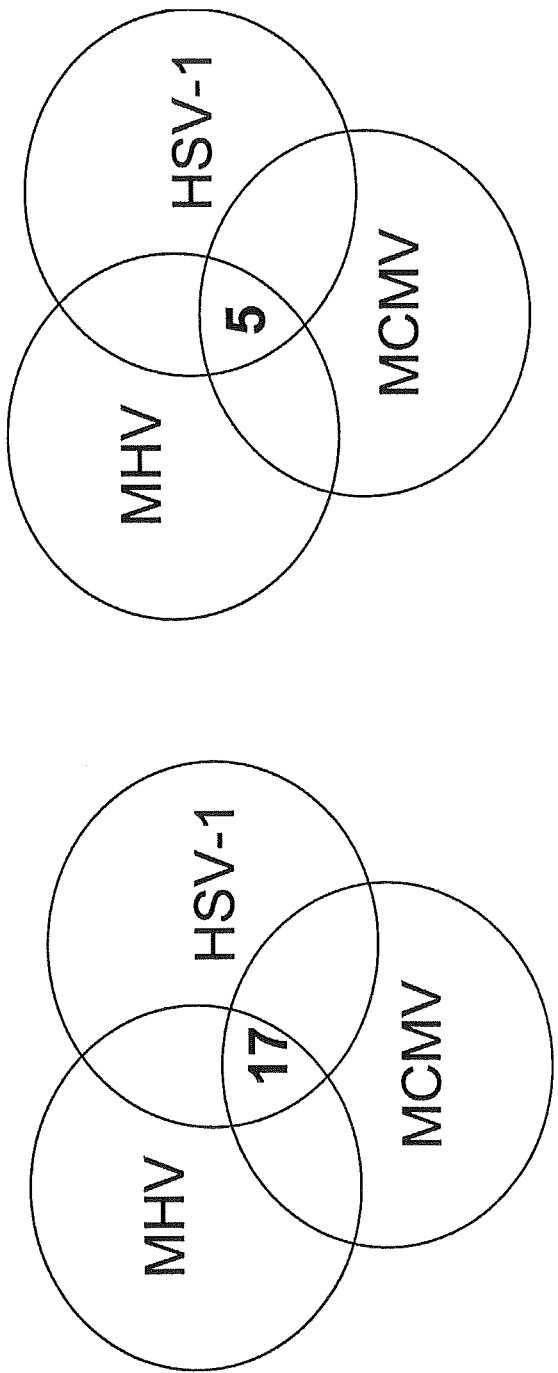
FIG. 7: Representation of broad spectrum anti-viral miRNAs. The same methods and cut-offs as described for FIG. 5 were used for 3 different viruses—MCMV, MHV-68 and HSV. A list of 21 mimics that had the same effect (down regulation) on all three viruses using these criteria was obtained. 1 family of microRNAs, mir-30, resulted in >1.5 fold up regulation of replication in all three viruses.

The microRNAs are tested in other cell types to determine whether they perform the same pro- or anti-viral functions. The screening (as described above) was done in NIH-3T3 (fibroblast) cells and C127 (epithelial) cells (see FIG. 7). The results of these screens show that a number of the microRNAs listed as SEQ ID NOS: 1-22 have the same anti- or pro-viral function in the different cell types. This is strong evidence that the miRNA host targets are expressed in the different cell types.

Validation in Human DNA Viruses

All of the microRNA hits identified in our screen have either a perfectly identical sequence in human, or at a minimum, a conserved seed site (nt 2-7)—(implying that the targets and function of these microRNAs are conserved in mouse and human).

Figure 9:
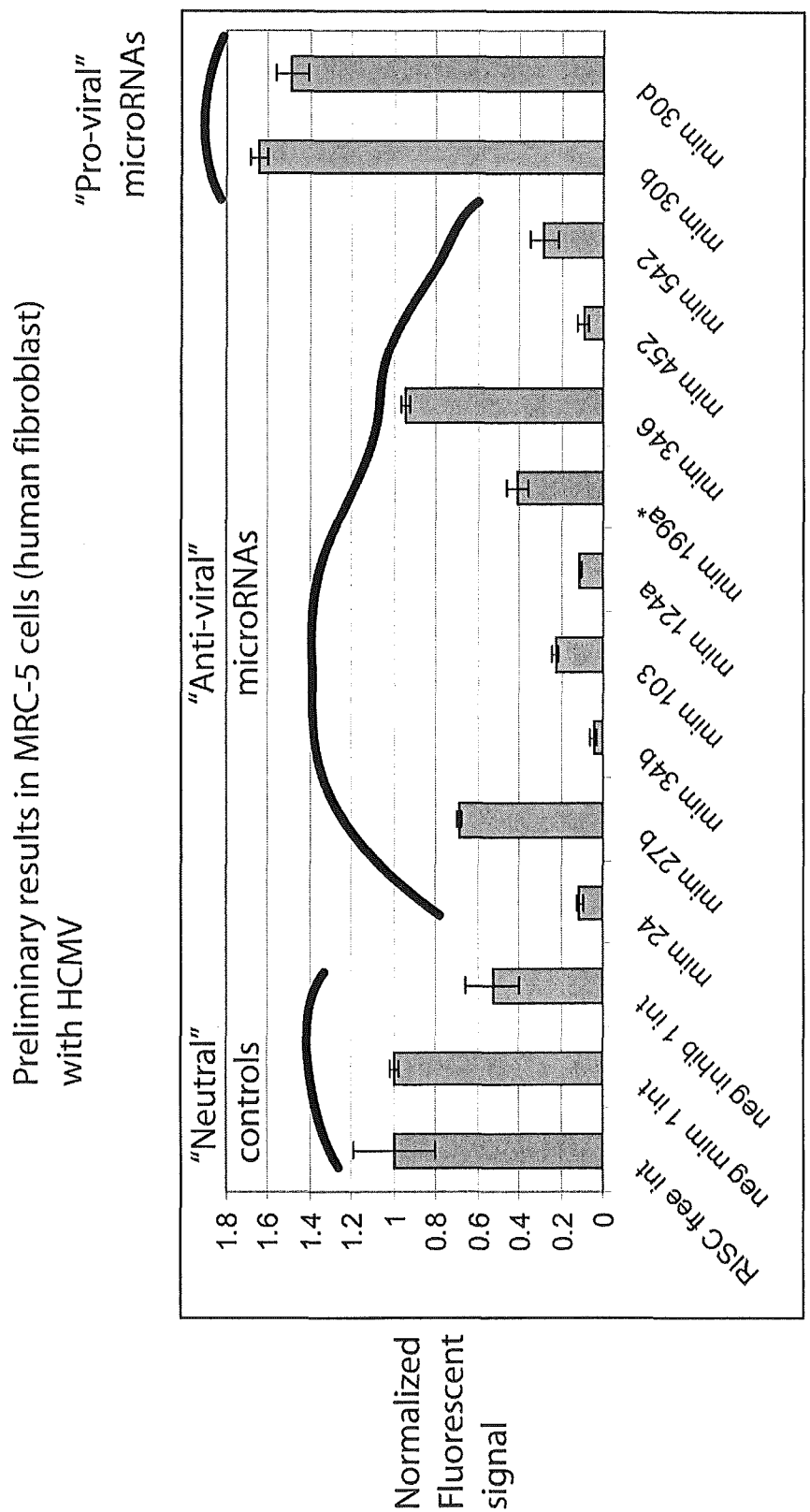
FIG. 9: Preliminary results in MRC-5 human fibroblasts infected with HCMV at an MOI of 0.5. Fluorescence was measured at 58 hrs post infection.
Figure 10:
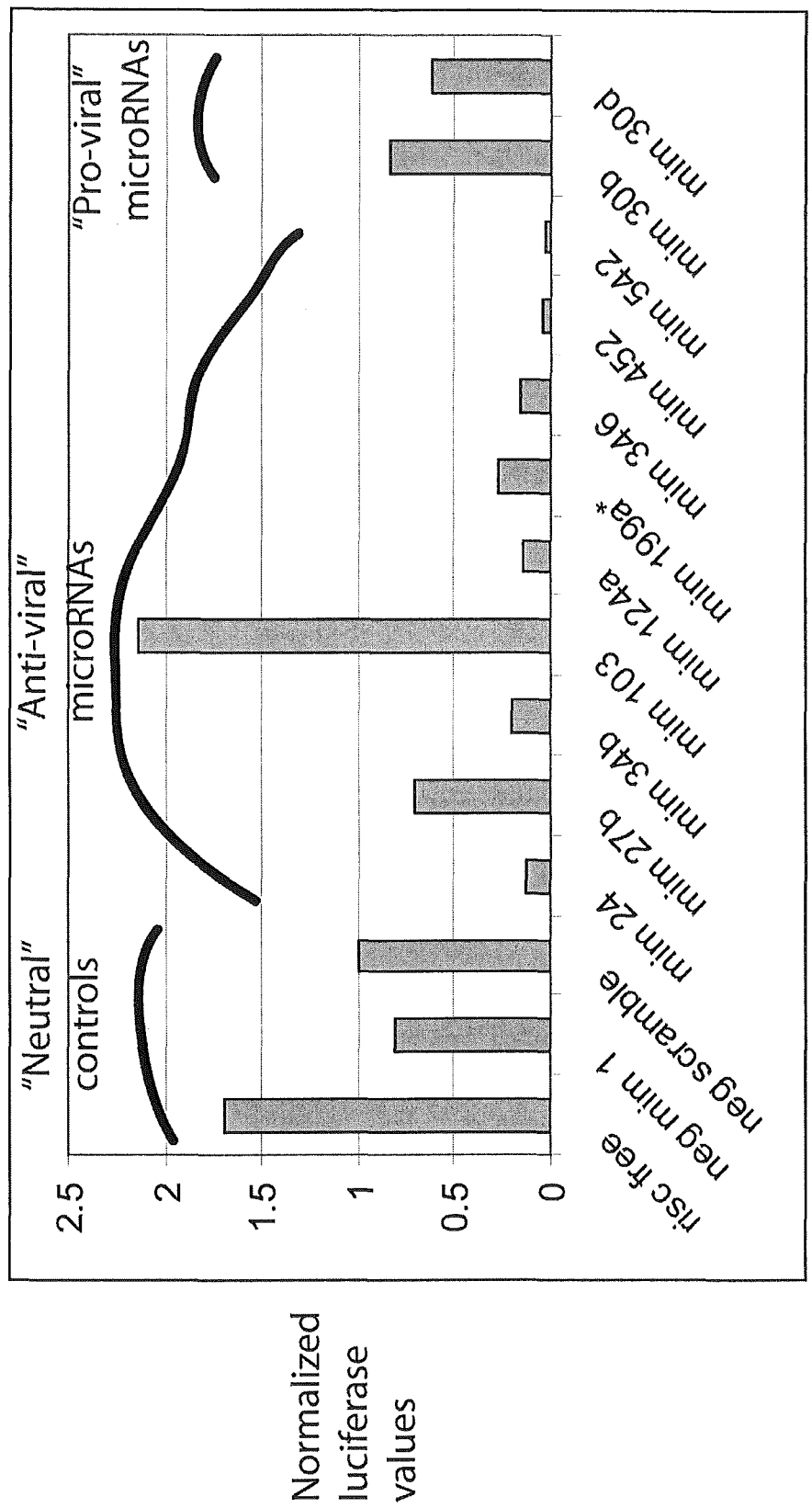
FIG. 10: Preliminary results in NIH-3T3 cells infected with SFV with luciferase reporter at an MOI of 0.5. Luciferase was measured at 10 hrs post infection.
Figure 11A:
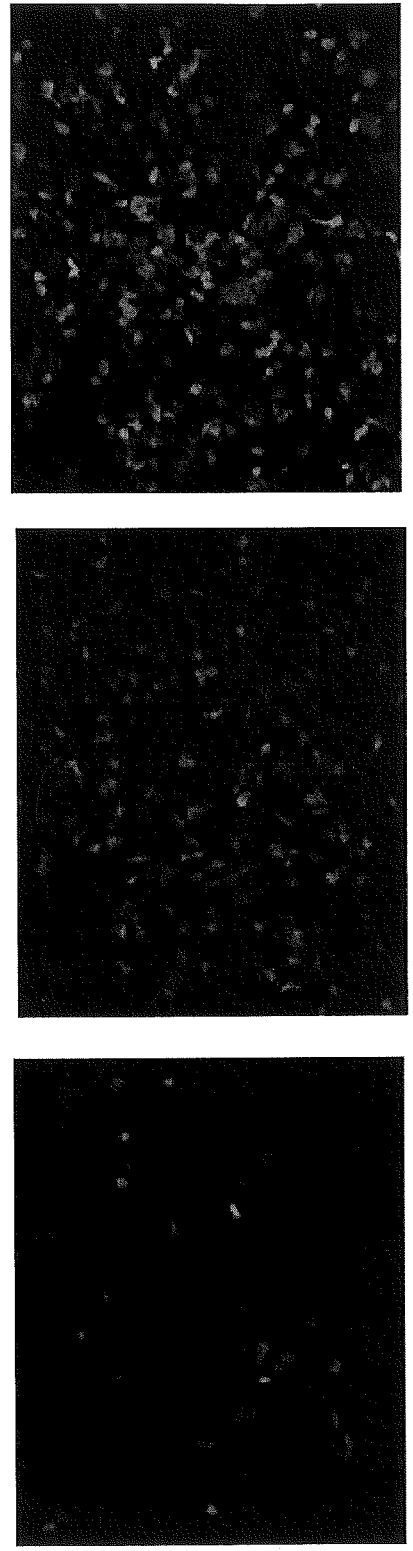
FIGS. 11A and 11B: NIH-3T3 cells were reverse transfected with 25 nm mir-30 inhibitor or mir-30 mimic for 48 hours prior to infection with MCMV (with GFP reporter).
Figure 11B:
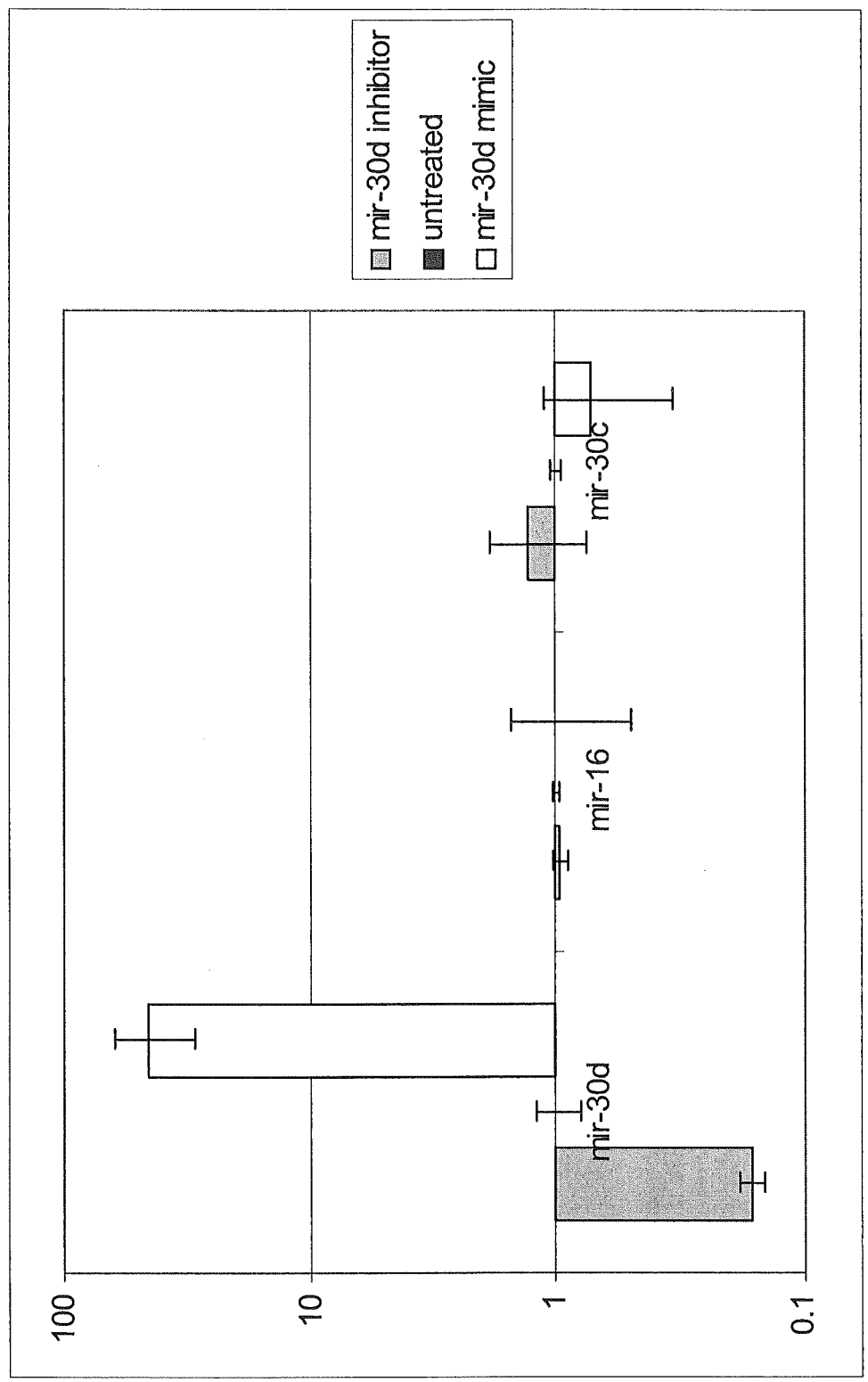
Figure 12A:
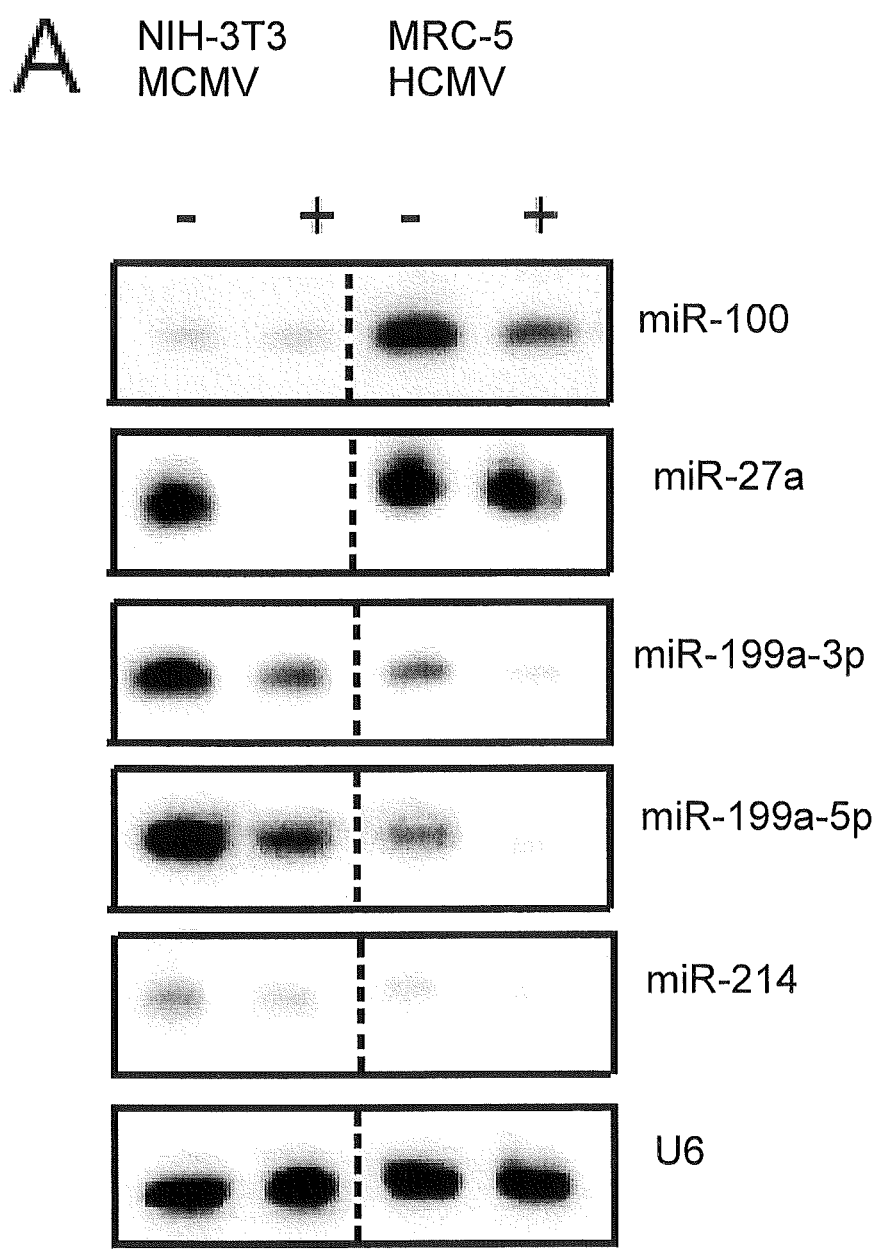
FIGS. 12A and 12B: Validation of anti- and pro-viral effects of miRNAs in human MRC-5 cells using HCMV.
Figure 12B:
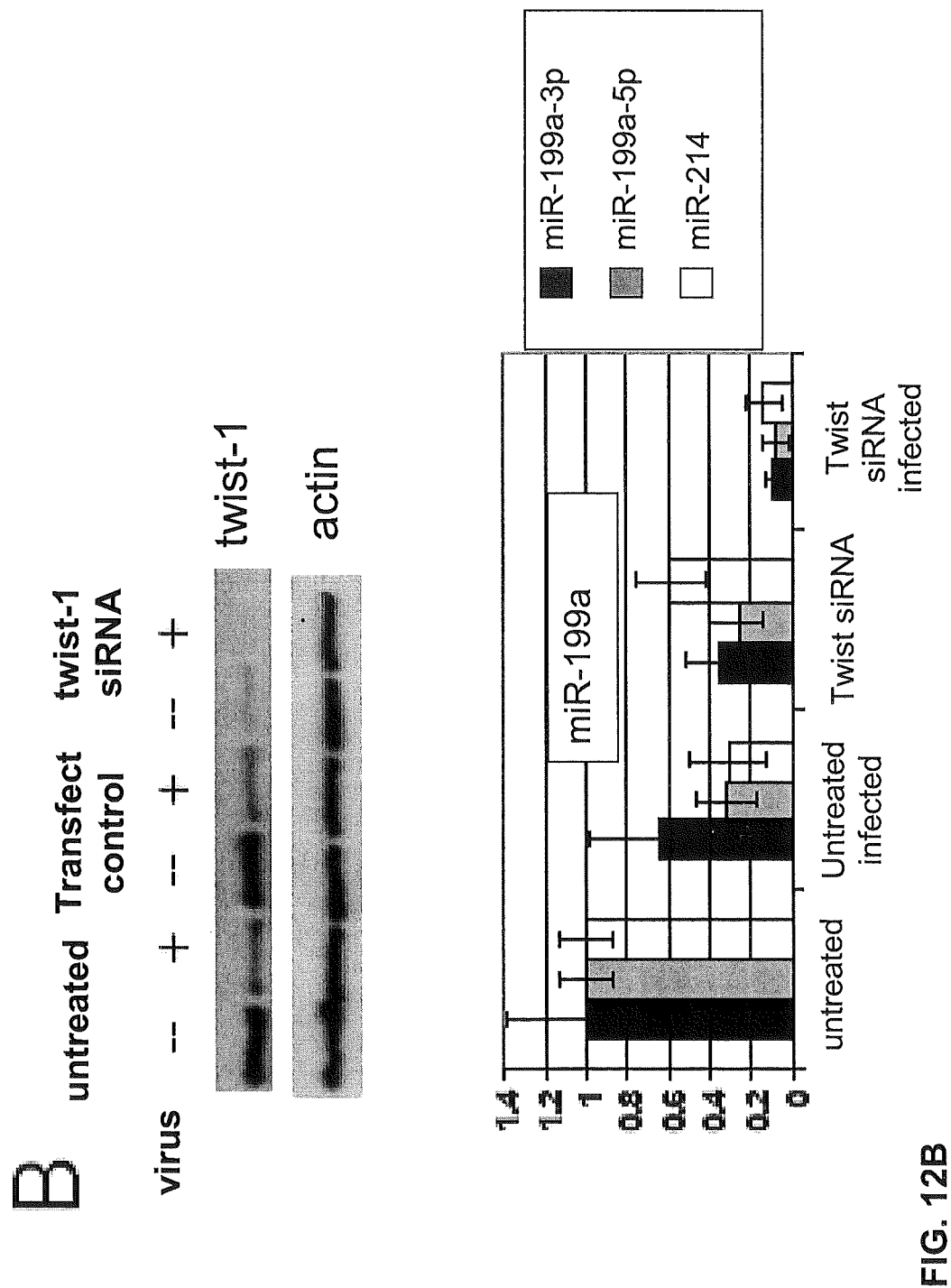

We have screened a number of the microRNAs listed in Table 1 and they have been identified as having the same anti- or pro-viral function in human cells with HCMV (see FIG. 9).

Validation in RNA Viruses

Figure 14:
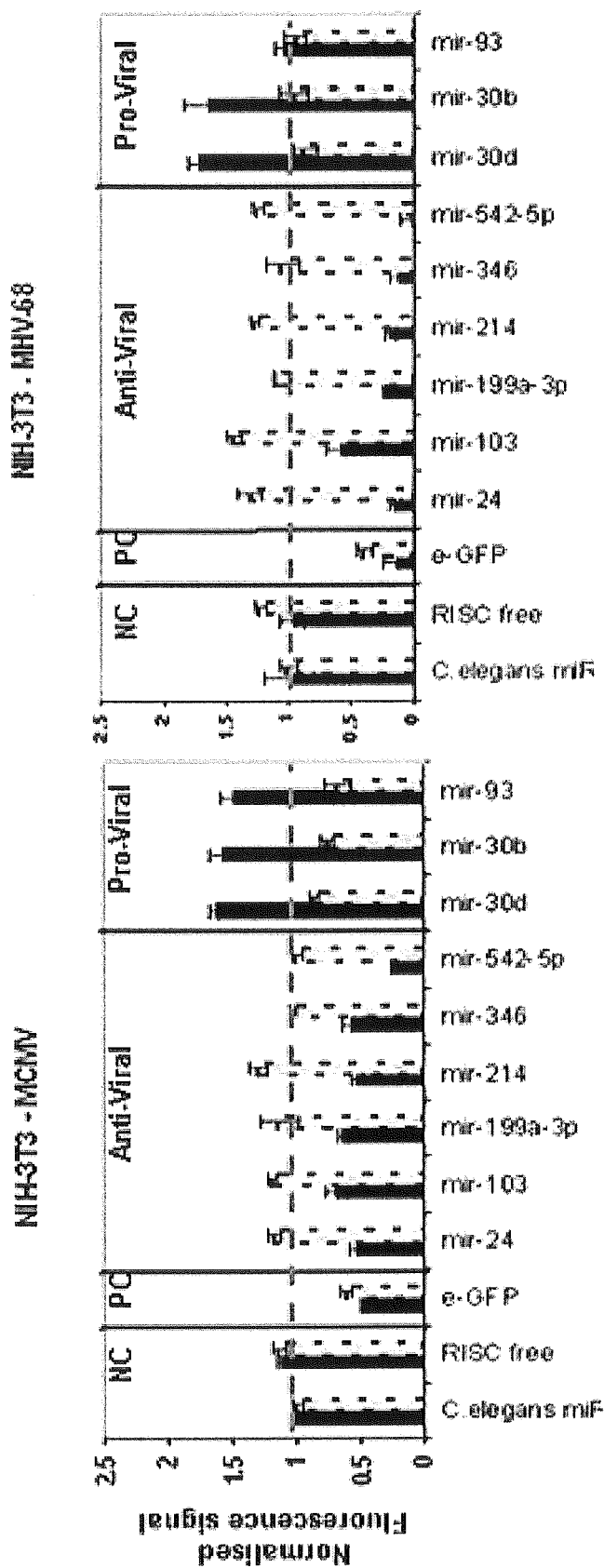
FIG. 14: Validation of anti- and pro-viral properties of miRNAs (individual and pooled) in both mouse and human cells.
Figure 14:
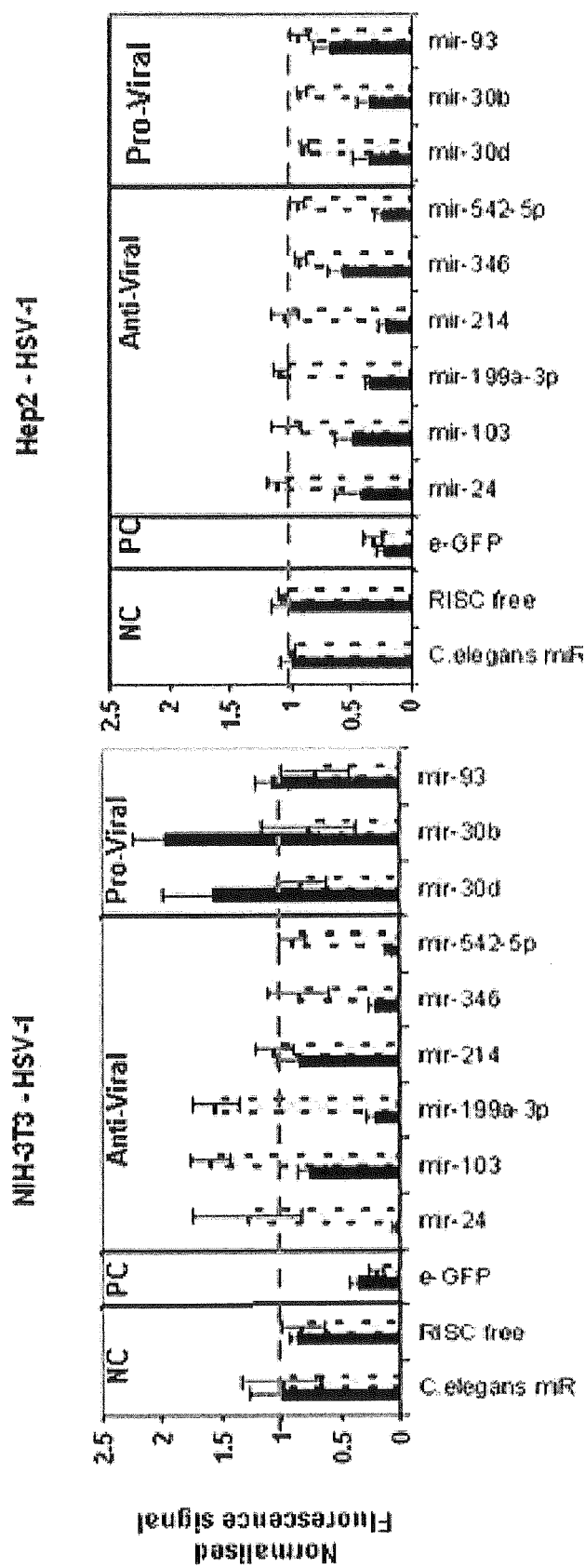
Figure 14:
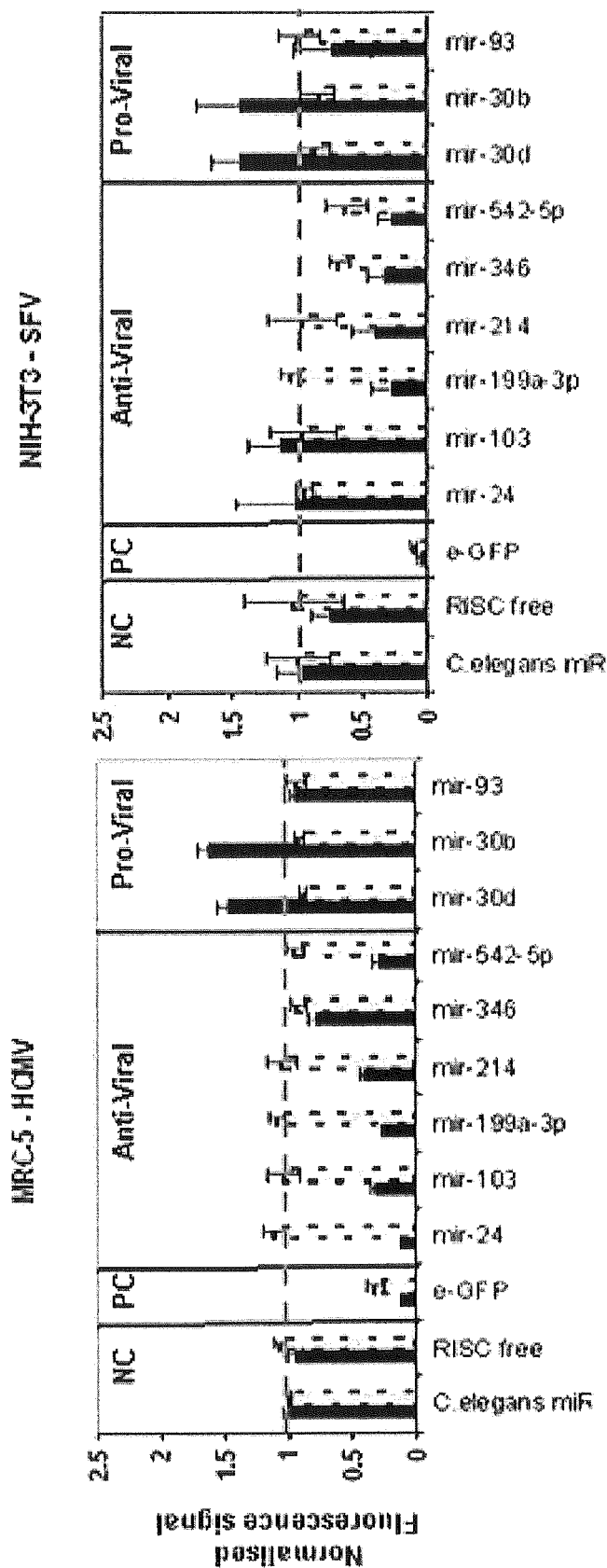
Figure 14:
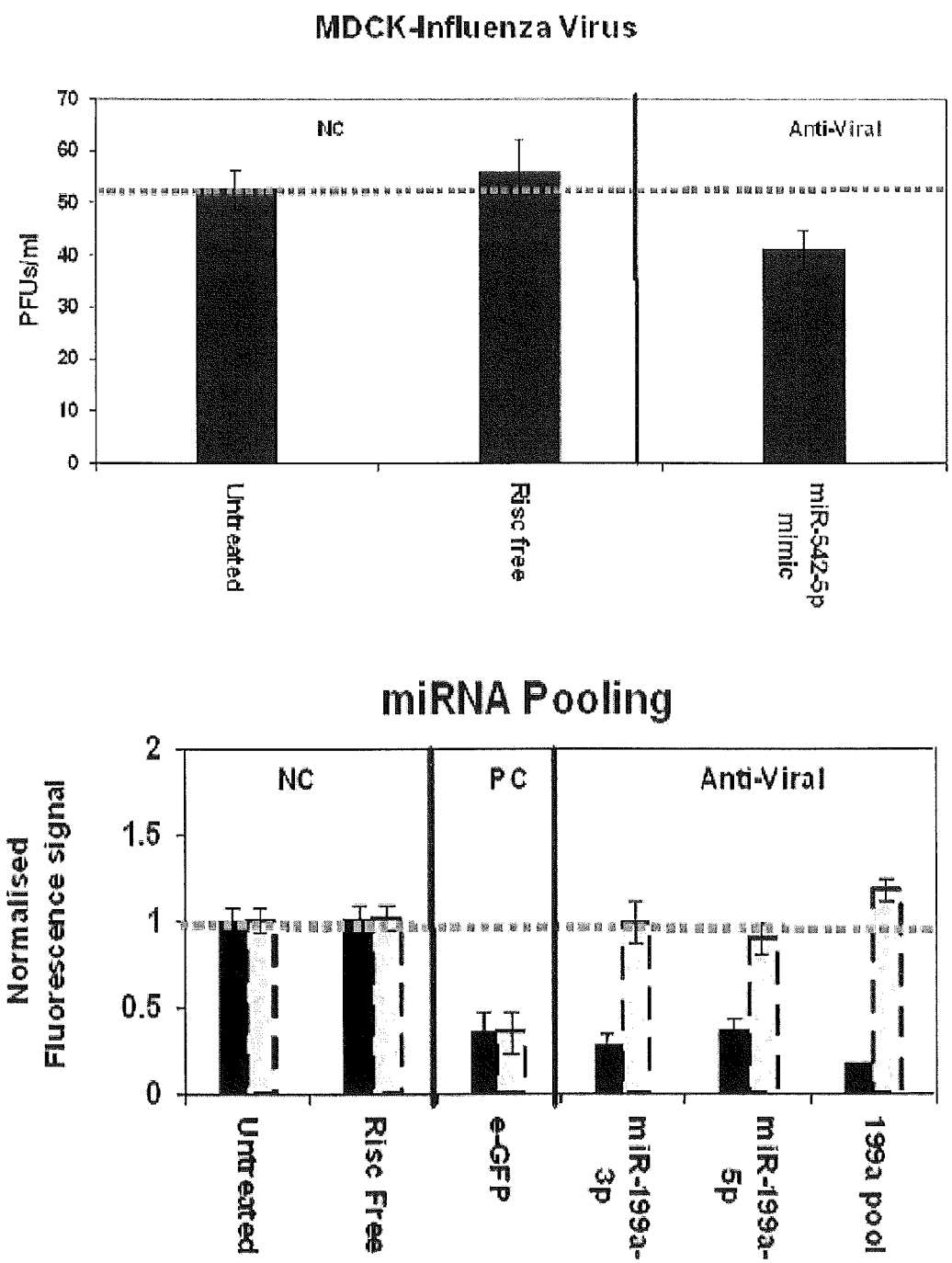
Figure 14:
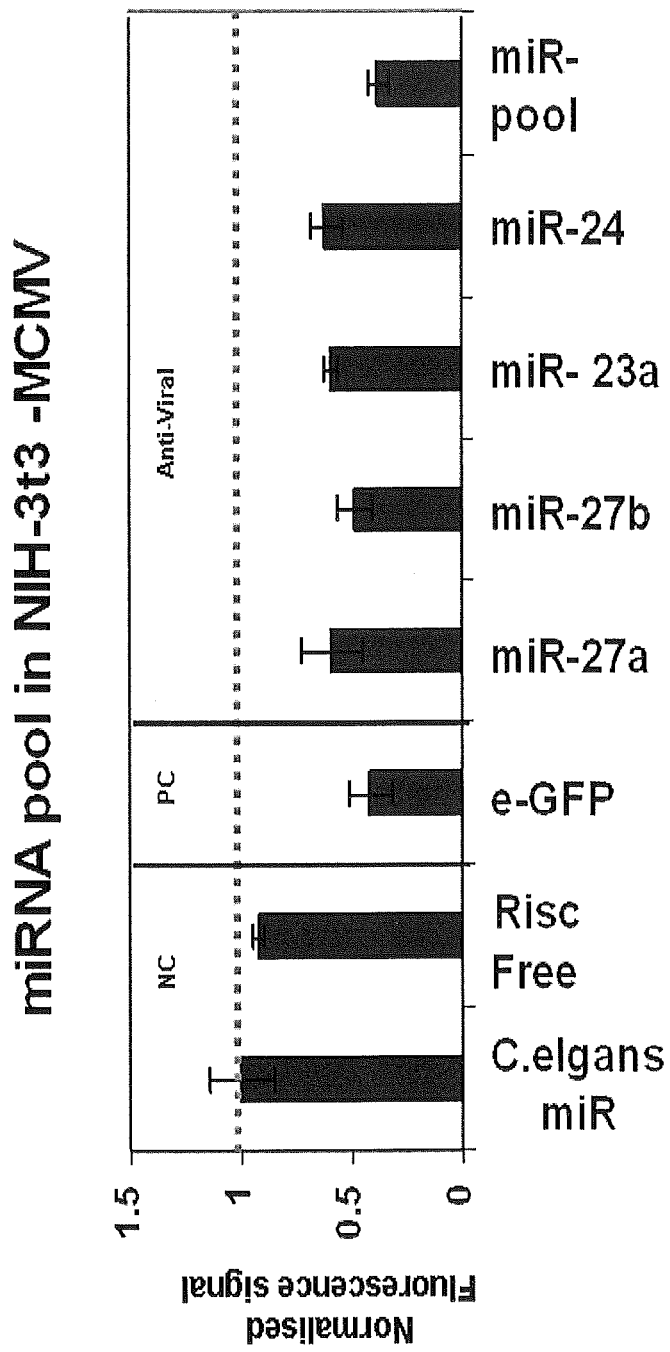

We have screened a number of the microRNAs listed as SEQ ID NOS: 1-22 and they show anti-viral microRNA function against Semliki-forest virus in NIH-3T3 cells.

miRNAs with Conserved Anti- or Pro-Viral Properties in all Three Herpesviral Subfamilies Mouse miRNAs that negatively impact viral growth in this assay are defined as those that lead to decreased fluorescence in the mimic library and increased fluorescence in the inhibitor library. A common metric for qualifying such "hits" is those that falls 1 or 2 standard deviations outside the mean of negative controls (reviewed in [20]). However, analysis of the mimic and inhibitor data suggests a stark difference in distributions and magnitude of effects. We therefore opted for the statistics-based hit selection method, "rank product", which does not make assumptions about underlying data distributions and is robust against outlier values [21]. "Hits" are defined as mimics or inhibitors that result in a consistently high or low fluorescent signal (in relation to all of the other mimics or inhibitors) and statistical weight is based on replication between experiments [21]. There is a clear correlation between the rank product p value and the change in fluorescence induced by a mimic or inhibitor (compared to negative controls). Using the combined datasets for all three viruses (n=19; FDR<0.01) rank product analysis identified 4 high-confidence anti-viral miRNAs (decreased fluorescence in the mimic library, increased fluorescence in the inhibitor library): miR-199a-3p, miR-214, miR-103 and miR-24 and 3 high-confidence pro-viral miRNAs (increased fluorescence in the mimic library, decreased fluorescence in the inhibitor library)—mir-30b, mir-30d and mir-93. With the exception of mir-93, all of these miRNAs validated in subsequent analysis (FIG. 14). Analysis of individual datasets revealed differences between viruses (e.g. mir-29b is strongly anti-viral in HSV-1 but not MCMV or MHV-68 and miR-378 is pro-viral in MCMV but not MHV-68 or HSV-1). To equate the change in fluorescent signal of these miRNA mimics and inhibitors with the change in quantity of infectious virus, standard plaque assays were performed with the wild-type MCMV virus. At 70 hours post infection the mimics result in a ~log-fold effect on quantity of infectious virus whereas inhibitors result in ~2 fold changes. Growth curve analysis further demonstrates 1-2 log fold decrease in infectious virus based on miR-199a-3p and miR-214 mimics and a ~5 fold increase in quantity of virus with the miR-30 mimic. Notably, these high confidence hits are perfectly conserved in mouse and human and the same anti- and pro-viral properties are observed when examining the human CMV virus in human cells. To gain perspective on the breadth of these anti- or pro-viral effects, we also examined Semiliki forest virus, an alphavirus that is evolutionary unrelated, using a replicon system which replicates in NIH-3T3 cells. As shown in FIG. 14, as with the herpesviruses, mir-199a-3p and miR-214 display anti-viral properties against SFV whereas miR-30 shows pro-viral properties.

Regulation of Host Signalling Networks by Mir-199a-3p.

Figure 13A:
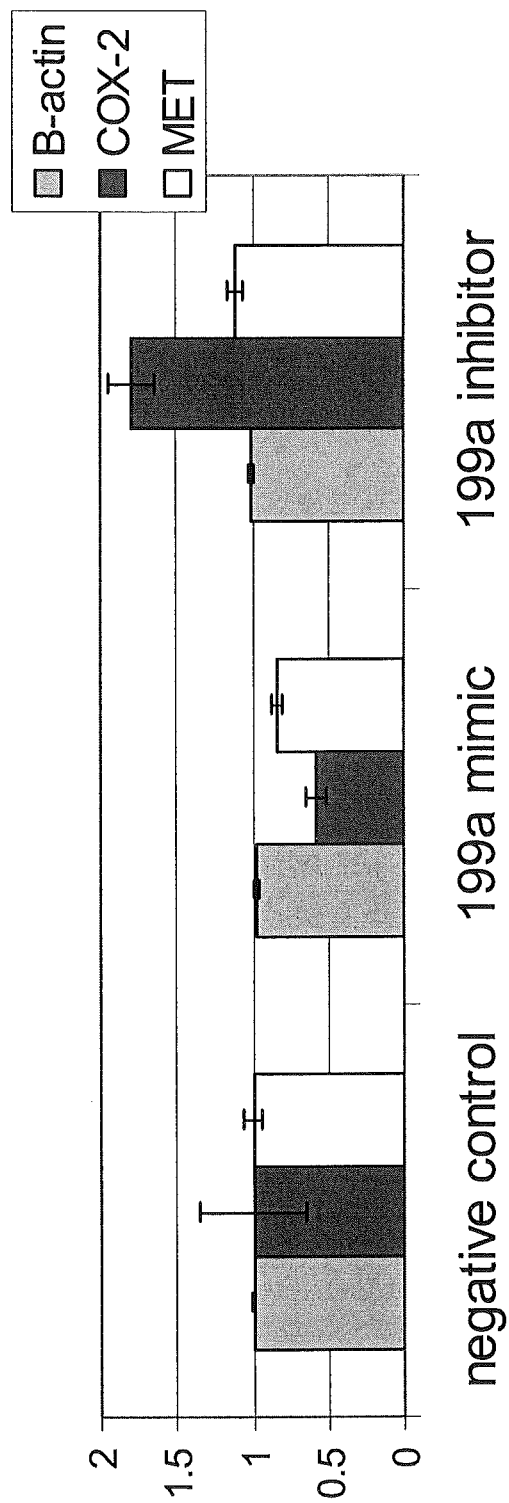
FIGS. 13A and 13B: COX-2 is down-regulated upon miR-199a-3p over-expression and is upregulated upon miR-199a-3p inhibition in both mouse (FIG. 13A) and human (FIG. 13B) cells.
Figure 13B:
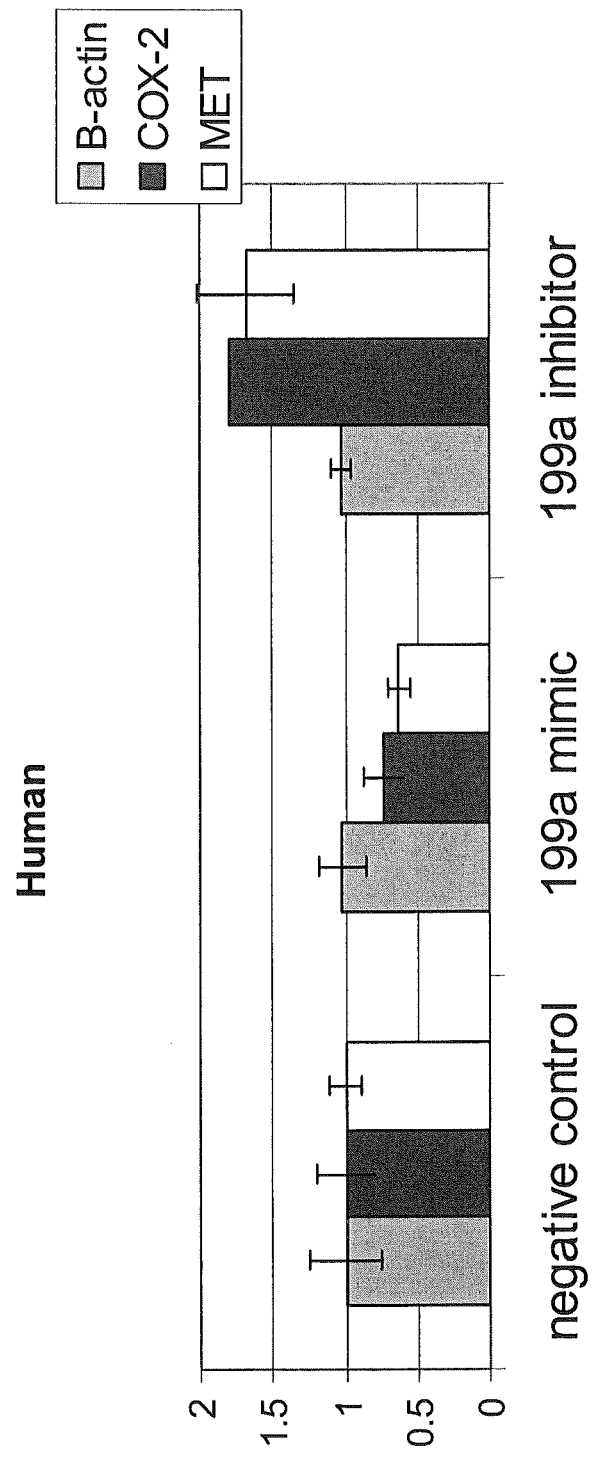
Figure 15:
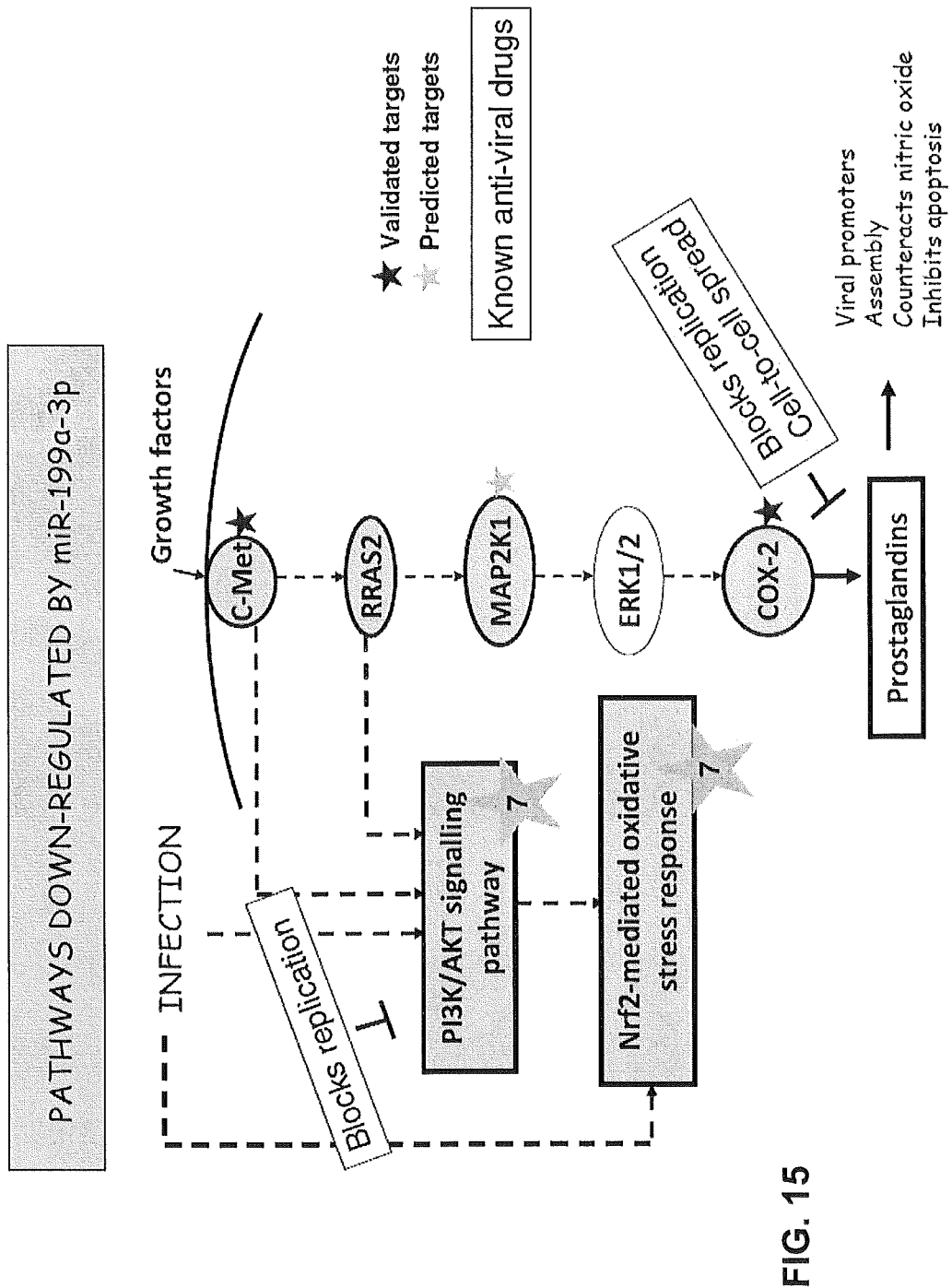
FIG. 15: Genes regulated by miR-199a. Accordingly, miRNAs can act as antivirals—regulating multiple networks, that are important/required for viral life cycles, simultaneously.

Given the large number of potential targets of any given miRNA (most recent estimates at ~300), it may not be that one specific target (or even a handful of targets) sufficiently explains a miRNA-based phenotype. For example, one of the previously reported targets of miR-199a-3p is the prostaglandin synthesis COX-2. Inhibition of this gene has already been shown as an anti-viral strategy in multiple herpesviruses and could potentially explain the anti-viral properties of miR-199a-3p. Consistent with this, COX-2 is down-regulated upon miR-199a-3p over-expression and is upregulated upon miR-199a-3p inhibition in both mouse and human cells (FIGS. 13A and 13B). However, COX-2 is reported to be targeted by several other miRNAs (e.g. miR-16, xx), which do not display the same anti-viral properties. To obtain an unbiased (and more holistic) view of the gene networks that might contribute to miR-199a-3p function, global transcription analysis was carried out with both over-expression and inhibition. FIG. 15 shows a list of the most significant genes and networks regulated by mir-199a-3p. Several of these are important to a number of viruses and have been shown to represent drug targets individually.

TABLE 1

Summary of data

| Priority | miRNA | MCMV 3T3 | MHV 3T3 | HSV-1 3T3 | SFV 3T3 | HCMV MRC-5 | HSV-1 HEP2 | INFLUENZA MDCK |
|---|---|---|---|---|---|---|---|---|
| 1 | miR-199a-3p | ✓ | ✓ | ✓ | ✓ | ✓ | ✓ | — |
| 2 | miR-214 | ✓ | ✓ | — | ✓ | ✓ | ✓ | n/a |
| 3 | miR-346 | ✓ | ✓ | ✓ | ✓ | — | ✓ | n/a |
| 4 | miR-542 | ✓ | ✓ | ✓ | ✓ | ✓ | ✓ | ✓ |
| 5 | miR-744 | ✓ | ✓ | ✓ | ✓ | ✓ | ✓ | n/a |
| 6 | miR-24 | ✓ | ✓ | ✓ | — | ✓ | ✓ | n/a |
| 7 | miR-103 | ✓ | ✓ | ✓ | — | ✓ | ✓ | n/a |
| 8 (but multiple) | mir-30 family inhibitors | ✓ | ✓ | ✓ | ✓ | ✓ | — | n/a |
| 9 | miR-452 | ✓ | ✓ | ✓ | ✓ | ✓ | ✓ | n/a |
| 10 | miR-27b | ✓ | ✓ | ✓ | — | ✓ | — | n/a |
| 11 | miR-155 | ✓ | ✓ | ✓ | ✓ | n/a | ✓ | n/a |
| 12 | miR-222 | ✓ | ✓ | ✓ | — | n/a | ✓ | n/a |
| 13 | miR-223 | ✓ | ✓ | ✓ | ✓ | n/a | ✓ | n/a |
| 14 | miR-345 | ✓ | ✓ | ✓ | ✓ | n/a | ✓ | n/a |
| 15 | miR-28 | ✓ | ✓ | ✓ | ✓ | n/a | — | n/a |

TABLE 1-continued

Summary of data

| Priority | miRNA | MCMV 3T3 | MHV 3T3 | HSV-1 3T3 | SFV 3T3 | HCMV MRC-5 | HSV-1 HEP2 | INFLUENZA MDCK |
|---|---|---|---|---|---|---|---|---|
| 16 | miR-107 | ✓ | ✓ | ✓ | n/a | n/a | n/a | n/a |
| 17 | miR-124a | ✓ | ✓ | ✓ | ✓ |  | ✓ | n/a |
| 18 | miR-128 | ✓ | ✓ | ✓ | — | n/a | ✓ | n/a |
| 19 | miR-129-5p | ✓ | ✓ | ✓ | — | n/a | ✓ | n/a |
| 20 | miR-30a-3p | ✓ | ✓ | ✓ | ✓ | n/a | ✓ | n/a |
| 21 | miR-34b | ✓ | ✓ | ✓ | ✓ | ✓ | ✓ | n/a |
| 22 | miR-16 | ✓ | ✓ | ✓ | ✓ | ✓ | ✓ | n/a |
| Pool 1 | 199a-3p/199a-5p/214 mimic pool | ✓ | n/a | n/a | n/a | ✓ | ✓ | n/a |
| Pool 2 | 23/24/27 mimic pool | ✓ | n/a | n/a | n/a | n/a | n/a | n/a |

REFERENCES

*The Following 7 References are Mentioned by Number in the Materials and Methods Section of the Detailed Description*.

1. Angulo, A., P. Ghazal, and M. Messerle, The major immediate-early gene ie3 of mouse cytomegalovirus is essential for viral growth. J Virol, 2000. 74(23): p. 11129-36.
2. Manning, W. C. and E. S. Mocarski, Insertional mutagenesis of the murine cytomegalovirus genome: one prominent alpha gene (ie2) is dispensable for growth. Virology, 1988. 167(2): p. 477-84.
3. Buck, A. H., et al., Discrete clusters of virus-encoded micrornas are associated with complementary strands of the genome and the 7.2-kilobase stable intron in murine cytomegalovirus. J Virol, 2007. 81(24): p. 13761-70.
4. Dutia, B. M., et al., Identification of a region of the virus genome involved in murine gammaherpesvirus 68-induced splenic pathology. J Gen Virol, 2004. 85(Pt 6): p. 1393-400.
5. Sunil-Chandra, N. P., et al., Virological and pathological features of mice infected with murine gamma-herpesvirus 68. J Gen Virol, 1992. 73 (Pt 9): p. 2347-56.
6. Sun, A., et al., Immediate-early expression of the herpes simplex virus type 1 ICP27 transcript is not critical for efficient replication in vitro or in vivo. J Virol, 2004. 78(19): p. 10470-8.
7. Breitling, R., et al., Rank products: a simple, yet powerful, new method to detect differentially regulated genes in replicated microarray experiments. FEBS Lett, 2004. 573 (1-3): p. 83-92.

*The Following 21 References are Mentioned by Number in the Results Section of the Detailed Description*

1. Chang, T. C. and J. T. Mendell, microRNAs in vertebrate physiology and human disease. Annu Rev Genomics Hum Genet, 2007. 8: p. 215-39.
2. Winter, J., et al., Many roads to maturity: microRNA biogenesis pathways and their regulation. Nat Cell Biol, 2009. 11(3): p. 228-34.
3. Buck, A. H., et al., Post-transcriptional regulation of miR-27 in murine cytomegalovirus infection. Rna. 16(2): p. 307-15.
4. Wang, F. Z., et al., Human cytomegalovirus infection alters the expression of cellular microRNA species that affect its replication. J Virol, 2008. 82(18): p. 9065-74.
5. Lecellier, C. H., et al., A cellular microRNA mediates antiviral defense in human cells. Science, 2005. 308 (5721): p. 557-60.
6. Otsuka, M., et al., Hypersusceptibility to vesicular stomatitis virus infection in Dicer1-deficient mice is due to impaired miR24 and miR93 expression. Immunity, 2007. 27(1): p. 123-34.
7. Parameswaran, P., et al., Six RNA viruses and forty-one hosts: viral small RNAs and modulation of small RNA repertoires in vertebrate and invertebrate systems. PLoS Pathog, 2010. 6(2): p. e1000764.
8. Jopling, C. L., et al., Modulation of hepatitis C virus RNA abundance by a liver-specific MicroRNA. Science, 2005. 309(5740): p. 1577-81.
9. Pedersen, I. M., et al., Interferon modulation of cellular microRNAs as an antiviral mechanism. Nature, 2007. 449(7164): p. 919-22.
10. Murakami, Y., et al., Regulation of the hepatitis C virus genome replication by miR-199a. J Hepatol, 2009. 50(3): p. 453-60.
11. Huang, J., et al., Cellular microRNAs contribute to HIV-1 latency in resting primary CD4+ T lymphocytes. Nat Med, 2007. 13(10): p. 1241-7.
12. Triboulet, R., et al., Suppression of microRNA-silencing pathway by HIV-1 during virus replication. Science, 2007. 315(5818): p. 1579-82.
13. Ahluwalia, J. K., et al., Human cellular microRNA hsa-miR-29a interferes with viral nef protein expression and HIV-1 replication. Retrovirology, 2008. 5: p. 117.
14. Nathans, R., et al., Cellular microRNA and P bodies modulate host-HIV-1 interactions. Mol Cell, 2009. 34(6): p. 696-709.
15. Martinez, I., et al., Human papillomavirus type 16 reduces the expression of microRNA-218 in cervical carcinoma cells. Oncogene, 2008. 27(18): p. 2575-82.
16. Yeung, M. L., et al., Roles for microRNAs, miR-93 and miR-130b, and tumor protein 53-induced nuclear protein 1 tumor suppressor in cell growth dysregulation by human T-cell lymphotrophic virus 1. Cancer Res, 2008. 68(21): p. 8976-85.

17. Mahajan, V. S., A. Drake, and J. Chen, Virus-specific host miRNAs: antiviral defenses or promoters of persistent infection? Trends Immunol, 2009. 30(1): p. 1-7.
18. Ghosh, Z., B. Mallick, and J. Chakrabarti, Cellular versus viral microRNAs in host-virus interaction. Nucleic Acids Res, 2009. 37(4): p. 1035-48.
19. McGeoch, D. J., et al., Molecular phylogeny and evolutionary timescale for the family of mammalian herpesviruses. J Mol Biol, 1995. 247(3): p. 443-58.
20. Birmingham, A., et al., Statistical methods for analysis of high-throughput RNA interference screens. Nat Methods, 2009. 6(8): p. 569-75.
21. Breitling, R., et al., Rank products: a simple, yet powerful, new method to detect differentially regulated genes in replicated microarray experiments. FEBS Lett, 2004. 573(1-3): p. 83-92.

*The References Below Appear Throughout the Specification*

Bartel, D. P. (2004). "MicroRNAs: genomics, biogenesis, mechanism, and function." Cell 116(2): 281-97.
Ghosh, Z., B. Mallick, et al. (2008). "Cellular versus viral microRNAs in host-virus interaction." Nucleic Acids Res.
Giraldez, A. J., Y. Mishima, et al. (2006). "Zebrafish MiR-430 promotes deadenylation and clearance of maternal mRNAs." Science 312(5770): 75-9.
Gottwein, E. and B. R. Cullen (2008). "Viral and cellular microRNAs as determinants of viral pathogenesis and immunity." Cell Host Microbe 3(6): 375-87.
Huang, J., F. Wang, et al. (2007). "Cellular microRNAs contribute to HIV-1 latency in resting primary CD4+ T lymphocytes." Nat Med 13(10): 1241-7.
Jopling, C. L., K. L. Norman, et al. (2006). "Positive and negative modulation of viral and cellular mRNAs by liver-specific microRNA miR-122." Cold Spring Harb Symp Quant Biol 71: 369-76.
Kumar, A. (2008). "RNA interference: a multifaceted innate antiviral defense." Retrovirology 5: 17.
Lecellier, C. H., P. Dunoyer, et al. (2005). "A cellular microRNA mediates antiviral defense in human cells." Science 308(5721): 557-60.
Lewis, B. P., C. B. Burge, et al. (2005). "Conserved seed pairing, often flanked by adenosines, indicates that thousands of human genes are microRNA targets." Cell 120(1): 15-20.
Mahajan, V. S., A. Drake, et al. (2008). "Virus-specific host miRNAs: antiviral defenses or promoters of persistent infection?" Trends Immunol.
Otsuka, M., Q. Jing, et al. (2007). "Hypersusceptibility to vesicular stomatitis virus infection in Dicer1-deficient mice is due to impaired miR24 and miR93 expression." Immunity 27(1): 123-34.
Triboulet, R., B. Mari, et al. (2007). "Suppression of microRNA-silencing pathway by HIV-1 during virus replication." Science 315(5818): 1579-82.

---

The invention claimed is:

1. A method of treating a subject having one or more viral infections, viral diseases and/or viral conditions, said method comprising the steps of administering to the subject a pharmaceutically effective amount of a multi-species antiviral microRNA (miRNA) capable of modulating or mimicking the expression, function and/or activity of a host cell miRNA molecule, wherein the host cell miRNA is miR-542 having the nucleotide sequence of SEQ ID NO: 13.

2. The method of claim 1, wherein the multi-species antiviral miRNA is effective against three or more viral species.

3. The method of claim 1, wherein the multi-species antiviral miRNA is miR-542 having the nucleotide sequence of SEQ ID NO: 13.

4. The method of claim 1, wherein the multi-species antiviral microRNA is introduced into a cell of the subject using a transfection protocol and/or a vector.

* * * * *

UNITED STATES PATENT AND TRADEMARK OFFICE
CERTIFICATE OF CORRECTION

PATENT NO. : 9,695,420 B2  
APPLICATION NO. : 14/467988  
DATED : July 4, 2017  
INVENTOR(S) : Buck It is certified that error appears in the above-identified patent and that said Letters Patent is hereby corrected as shown below:

On the Title Page

(56) References Cited, Other Publications, left column, Cullen:  
Please correct "38:525-530" to read -- 38: S25-S30 --

Other Publications, left column, Gottwein et al.:  
Please correct "Viral Patnogenesis" to read -- Viral Pathogenesis --

In the Specification

Column 2, Line 18: Please correct "(Mahaj an, Drake" to read -- (Mahajan, Drake --

Column 13, Lines 53 and 60: Please correct "LHAgfp" to read -- LH$\Delta$gfp --

Signed and Sealed this  
Twenty-second Day of May, 2018

Andrei Iancu  
*Director of the United States Patent and Trademark Office*